(12) United States Patent
Sanchez et al.

(10) Patent No.: US 8,853,448 B2
(45) Date of Patent: Oct. 7, 2014

(54) AROMATIC SULFONYLIMIDES, PREPARATION THEREOF AND USE THEREOF AS ELECTROLYTE

(75) Inventors: Jean-Yves Sanchez, Saint-Ismier (FR); Bernard Langlois, Lyons (FR); Maurice Medebielle, Caluire et Cuire (FR); Fabien Toulgoat, Le Relecq Kerhuon (FR); Fannie Alloin, Vizille (FR); Elie Paillard, Strasbourg (FR); Cristina Iojoiu, Grenoble (FR)

(73) Assignees: Institut National Polytechnique de Grenoble, Grenoble (FR); Eras-Labo, Saint-Nazaire-les-Eymes (FR); Universite Claude Bernard Lyon, Villeurbanne (FR)

( * ) Notice: Subject to any disclaimer, the term of this patent is extended or adjusted under 35 U.S.C. 154(b) by 1662 days.

(21) Appl. No.: 12/309,462

(22) PCT Filed: Jul. 17, 2007

(86) PCT No.: PCT/FR2007/001225
§ 371 (c)(1),
(2), (4) Date: Nov. 2, 2009

(87) PCT Pub. No.: WO2008/009814
PCT Pub. Date: Jan. 24, 2008

(65) Prior Publication Data
US 2010/0174113 A1    Jul. 8, 2010

(30) Foreign Application Priority Data

Jul. 17, 2006   (FR) ..................... 06 06469

(51) Int. Cl.
| | | |
|---|---|---|
| C07C 303/00 | (2006.01) | |
| C07F 7/08 | (2006.01) | |
| H01M 10/0525 | (2010.01) | |
| C07C 317/14 | (2006.01) | |
| H01M 6/16 | (2006.01) | |
| H01M 6/18 | (2006.01) | |
| C07C 323/67 | (2006.01) | |
| H01G 11/62 | (2013.01) | |
| H01G 9/022 | (2006.01) | |
| H01M 10/0565 | (2010.01) | |
| H01M 10/0566 | (2010.01) | |
| H01M 6/06 | (2006.01) | |

(52) U.S. Cl.
CPC ............ C07C 323/67 (2013.01); C07F 7/0818 (2013.01); H01M 10/0525 (2013.01); C07C 317/14 (2013.01); H01M 6/166 (2013.01); H01M 6/183 (2013.01); H01M 6/188 (2013.01); H01M 6/06 (2013.01); H01G 11/62 (2013.01); H01M 6/181 (2013.01); H01G 9/038 (2013.01); H01M 10/0565 (2013.01); Y02E 60/122 (2013.01); Y02E 60/13 (2013.01); H01M 10/0566 (2013.01)
USPC ............................................. 564/82; 564/97

(58) Field of Classification Search
CPC .. C07C 311/48; C07C 311/29; C07C 303/38; C07C 303/28; C07C 323/67
USPC ...................................................... 564/82, 97
See application file for complete search history.

(56) References Cited

U.S. PATENT DOCUMENTS

| | | | |
|---|---|---|---|
| 5,514,493 A | 5/1996 | Waddell et al. ............... | 429/199 |
| 2001/0021790 A1 * | 9/2001 | Yonezawa et al. .............. | 564/80 |

FOREIGN PATENT DOCUMENTS

| | | | |
|---|---|---|---|
| EP | 0364340 | 4/1990 | ............ C07C 303/36 |
| EP | 1635218 | 3/2006 | .............. G03F 7/004 |

OTHER PUBLICATIONS

Sanchez; Journal of Fluorine Chemistry; 2011, 132, 1213-1218.*
International Search Report dated Nov. 22, 2007.

* cited by examiner

Primary Examiner — Sudhakar Katakam
Assistant Examiner — Pancham Bakshi
(74) Attorney, Agent, or Firm — Sofer & Haroun, LLP

(57) ABSTRACT

The invention relates to a process for preparing aromatic sulfonylimides, to the sulfonylimides obtained, and to the use thereof as salt of an electrolyte. The sulfonylimides correspond to the formula $[R-SO_2-N-SO_2R']_rM$ (I). R' is an ArZL- group. R' is a perfluoroalkyl group or an ArZL- group. Z is an S, SO or $SO_2$ group. L is a $-(CF_2)_n-CFR^f-$ group. n is 0 or 1; $R^f$ represents F or a $C_1$ to $C_8$ perfluoroalkyl group; Ar is an aromatic group. M represents H, an alkali metal cation, an alkaline earth metal cation, a trivalent or tetravalent metal cation, or an organic cation. The process consists in preparing a compound $RSO_2N(R')SO_2R'$ from $RSO_2F$, and in replacing the group R' by nucleophilic substitution reaction so as to obtain the compound (I), R' being a benzyl or trimethylsilyl group.

8 Claims, 2 Drawing Sheets

AROMATIC SULFONYLIMIDES, PREPARATION THEREOF AND USE THEREOF AS ELECTROLYTE

RELATED APPLICATIONS

This application is a National Phase application of PCT/FR2007/001225, filed on Jul. 17, 2007, which in turn claims the benefit of priority from French Patent Application No. 06 06469, filed on Jul. 17, 2006, the entirety of which are incorporated herein by reference.

FIELD OF THE INVENTION

The present invention relates to a method of preparing sulfonylimides, the sulfonylimides obtained and also their use as an electrolyte.

BACKGROUND OF THE INVENTION

It is known to use lithium bis(fluorosulfonyl)imides as salts for the electrolyte in various electrochemical devices, especially in batteries. The compounds that are the most representative are compounds of the type $(R_FSO_2)_2NM$ in which $R_F$ is a perfluoroalkyl group and M is an alkali metal cation or organic cation. These compounds have properties that are relatively good but that are however insufficient.

It is known to prepare sulfonylimides [$RSO_2NSO_2R'$]M by reaction of a sulfonyl fluoride $RSO_2F$ with a sulfonamide $R'SO_2NH_2$. However, the condensation reaction is in competition with a hydrolysis and the sulfonylimide is obtained with a low yield. Moreover, it is very difficult to modify the R group which has an electron-withdrawing nature (with a view to giving it additional properties, enabling for example grafting or polymerization) without degrading the sulfonimide group.

OBJECT AND SUMMARY OF THE INVENTION

The object of the present invention is to provide a new method of preparing functionalized sulfonylimides.

Consequently, the subject of the present invention is a method of preparing sulfonylimides, the sulfonylimides obtained, N-benzylsulfonimides as synthesis intermediates, and the use of sulfonylimides in electrochemical devices.

The method of the invention is intended for preparing sulfonylimides corresponding to the formula [R—$SO_2$—N—$SO_2R'$]$_r$M (I), and it consists in preparing an N-substituted sulfonimide $RSO_2N(R'')SO_2R'$ (II) from $RSO_2F$ (III), and in replacing the R" group via a nucleophilic substitution reaction in order to obtain the sulfonylimide (I), R" being a benzyl or trimethylsilyl group, it being understood that, in the formulae (I), (II) and (III):

R represents a group corresponding to the formula Ar—Z-L-;

R' represents a linear or branched perfluoroalkyl group, preferably a $CF_3$ or $C_2F_5$ group, or an Ar—Z-L- group;

Z represents a sulfide, sulfinyl or sulfonyl group;

L represents a group of formula —$(CF_2)_n$—$CFR^f$—;

n is 0 or 1;

$R^f$ represents F or a perfluoroalkyl group having from 1 to 8 carbon atoms;

Ar and where appropriate Ar' each represent an aromatic group chosen from the group constituted by monocyclic aromatic groups; polycyclic aromatic groups having fused or unfused rings; and heterocyclic aromatic groups that are bicyclic with fused or unfused rings or monocyclic; and M is a cation of valence r, chosen from alkali metal, alkaline-earth metal or trivalent or tetravalent metal cations and organic cations chosen from ammonium, phosphonium, imidazolium, guanidinium, piperidinium, pyrrolidinium, pyridinium or quinolinium ions.

The method of preparing the N-substituted sulfonylimide $RSO_2N(R'')SO_2R'$ (II) from the sulfonyl fluoride $RSO_2F$ (III) depends on the nature of the R' group.

When the R' group is a group identical to the Ar—Z-L group that constitutes R, the compound (II) is obtained by reaction of the compound R—$SO_2F$ with a hexamethyldisilazane salt $(Me_3Si)_2N^-A^+$ (A being an alkali metal cation or a quaternary ammonium ion) and it corresponds to the formula $RSO_2N(SiMe_3)SO_2R$ (IIa). The reaction may be carried out in THF. The reaction releases the fluoride AF which immediately generates the nucleophilic substitution on the compound II with replacement of the trimethylsilyl group by the cation $A^+$, with production of the symmetrical sulfonimide [(Ar—Z-L-$SO_2$) N]$_2$A.

When R' is a perfluoroalkyl group, the compound (II) corresponds to the formula $RSO_2N(R'')SO_2R'$ (IIb), R" being a benzyl group or an allyl group, and it is obtained via a compound $RSO_2NH(R'')$ (II'b). The method of preparing the compound (IIb) comprises the preparation of the compound (II'b) via reaction of R—$SO_2F$ (III) with benzylamine or allylamine in excess, then the neutralization by HCl and the separation of (II'b), then the reaction of the compound (II'b) with the anhydride $(R'SO_2)_2$—O, in the presence of a tertiary amine, for example diisopropylethylamine (DIEA). The reaction may be carried out in dichloroethane. The overall process may be represented by the following reaction scheme:

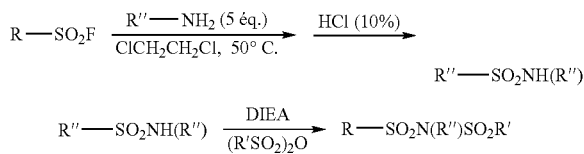

The reactant that reacts, preferably in the presence of an alcohol (for example ethanol) with an N-substituted sulfonylimide (IIb) for the nucleophilic substitution during the second step may be chosen from:

alkali metal or alkaline-earth metal hydroxides and halides, in order to obtain metallic sulfonimides;

quaternary ammonium ion hydroxides and halides, in order to obtain quaternary ammonium ion sulfonimides;

alkali metal or alkaline-earth metal alcoholates, in order to obtain metallic sulfonimides;

quaternary ammonium alcoholates, in order to obtain quaternary ammonium ion sulfonimides;

alkali metal or alkaline-earth metal amides, in order to obtain metallic sulfonimides;

quaternary ammonium amides, in order to obtain quaternary ammonium ion sulfonimides;

secondary amines, in order to obtain tertiary ammonium ion sulfonimides, one of the substituents of which is a benzyl group; and tertiary amines, in order to obtain quaternary ammonium ion sulfonimides, one of the substituents of which is a benzyl group. In the prior art, dissymmetrical sulfonimides are usually prepared by reaction of a sulfonyl fluoride with a sulfonamide $R_FSO_2NH_2$ or its silylated derivative $R_FSO_2N(Na)SiMe_3$ according to the following reactions:

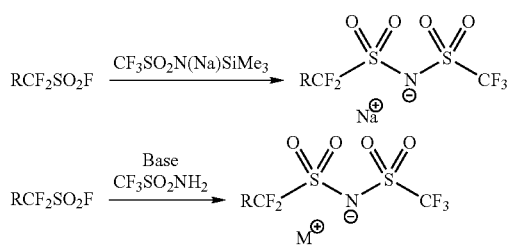

However, the reactants used are hygroscopic and poor nucleophilic reactants. Thus, if the reaction is not carried out under strictly anhydrous conditions, a hydrolysis reaction is in competition with the reaction for formation of the sulfonylimides with formation of sulfonate, which is very difficult to remove.

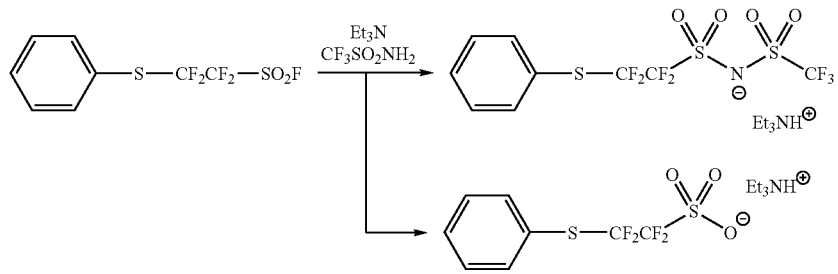

The method of the present invention, which combines a preliminary coupling reaction of a sulfonyl fluoride with benzylamine (which is a better nucleophile than $R_fSO_2NH_2$), enables a significantly greater selectivity than conventional coupling with $R_fSO_2NH_2$. The hydrolysis reaction that produces benzylammonium sulfonate becomes the minor reaction under these conditions, and the widely predominant reaction corresponds to the following reaction scheme:

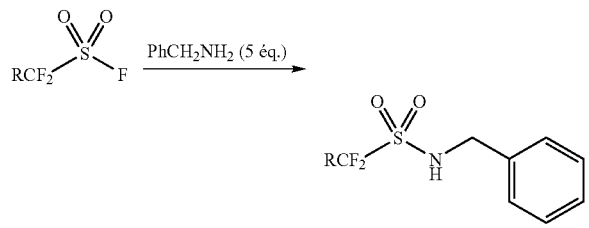

Furthermore, the purification of N-benzylsulfonamides is much easier than that of sulfonylimides. Moreover, the following conversions (formation of N-benzylsulfonimide, then deprotection in alcohol) are very selective and the by-products generated are very easily removed.

When the cation of the sulfonylimide is an organic cation, it may bear one or more substituents chosen independently from one another from:
hydrogen;
alkyl groups;
monocyclic aromatic groups; polycyclic aromatic groups having fused or unfused rings; heterocyclic aromatic groups in which the heteroatom is a nitrogen atom, said heterocyclic groups being polycyclic with fused or unfused rings or monocyclic.

As particular examples of organic cations, mention may be made of dialkylammonium and trialkylammonium cations, for example $(C_2H_5)_2NH_2^+$, $(C_2H_5)_3NH^+$, $(C_4H_9)_2NH_2^+$ and $(C_4H_9)_3NH^+$.

An aromatic Ar or Ar' group may be part of a repeat unit of a polymer chain.

The Ar group may bear one or more substituents chosen from:
halogen atoms, $Cl-CH_2-$, and $Q^1-O-CH_2-$ groups in which $Q^1$ is H, an alkyl group or an acyl group;
a hydroxyl group, ether $Q^2-O-$, carboxylic ester $Q^2C(O)O-$ and sulfonate $Q^2-SO_2-O-$ groups, $Q^2$ representing an alkyl group or an aryl group, [for example the benzyl ether $PhCH_2O-$, trityl ether $Ph_3CO-$, methyl ether $CH_3C-$, benzoyl ester $PhC(O)O-$ and acetyl ester $CH_3C(O)O-$];
aliphatic or aromatic groups having an optionally substituted ethylenic unsaturation [originating, for example, from a vinyl unit ($CH=CH_2-$), an allyl unit ($CH_2=CH-CH_2-$) or an acryloyloxy unit ($CH_2=CH-C(O)-O-$)];
the amino-$N(Q^3)(Q^4)$- groups in which $Q^3$ and $Q^4$ each represent, independently of one another, H, an alkyl group, an aryl group, an arylalkyl group or an acyl group, [for example $CH_3C(O)NH-$ or $PhCH_2NH-$];
trialkylsilyl groups;
oxirane groups; and
electron-withdrawing groups such as perfluoroalkyl groups, alkylsulfonyl or arylsulfonyl groups, sulfonyl halide groups, and ester, nitrile, cyclic carbonate or nitro groups.

A first family of sulfonylimides comprises the compounds corresponding to the formula (I) in which M is a monovalent cation, and R' is Ar—Z-L. These symmetrical compounds correspond to the formulae:

-(Ar-S-L-SO$_2$)$_2$N$^-$M$^+$        (Ia$_S$);

-(Ar—SO-L-SO$_2$)$_2$N$^-$M$^+$        (Ia$_{SO}$);

-(Ar—SO$_2$-L-SO$_2$)$_2$N$^-$M$^+$        (Ia$_{SO2}$).

A second family of sulfonylimides comprises the compounds that correspond to the formula (I) in which R' is a perfluoroalkyl group $C_pF_{2p+1}$, p preferably being from 1 to 8, more particularly from 1 to 2, namely [Ar—Z-L-SO$_2$—N—SO$_2$C$_p$F$_{2p+1}$]$_r$M (Ib).

A third family of sulfonylimides comprises the compounds that correspond to the formula (I) in which L is $CF_2$ or $(CF_2)_2$, namely [Ar—Z—(CF$_2$)$_2$—SO$_2$—N—SO$_2$R']$_r$M (Ic) and [Ar—Z—CF$_2$—SO$_2$—N—SO$_2$R']$_r$M (Ic').

A fourth family of sulfonylimides comprises the compounds (Id) that correspond to the formula (I) in which Ar is part of a repeat unit of a polymer chain.

A fifth family of sulfonylimides comprises the compounds that correspond to the formula (I) in which M is a monovalent cation and which correspond to the formula $(Ar-Z-L-SO_2)N(SO_2-R')^-M^+$ (Ie). Among the Ie compounds, mention may in particular be made of:
- lithium sulfonylimides $Ie_{Li}$;
- ammonium sulfonylimides $Ie_{amm}$ in which the ion is a quaternary ammonium;
- ammonium sulfonylimides $Ie_{ah}$ in which the ammonium ion bears at least one H atom; and
- imidazolium sulfonylimides $Ie_{im}$.

A sixth family of sulfonylimides comprises the compounds in which the cation M is divalent, namely the compounds $(Ar-Z-L-SO_2-N-SO_2R')^-{}_2M^{2+}$ (If). Mention may in particular be made of calcium sulfonylimides $If_{ca}$ and magnesium sulfonylimides $If_{mg}$.

A seventh family of sulfonylimides comprises the compounds (Ig) that correspond to the formula (I) in which Ar represents a phenyl group optionally bearing at least one substituent, in particular a phenyl group without a substituent, or a group bearing a substituent chosen from:
- halogens (for example Br or F);
- trialkylsilyls (for example trimethylsilyl);
- the hydroxyl group and ether (for example the benzyloxy group $PhCH_2O-$, the triphenyloxy group $Ph_3CO-$, the methyloxy group $CH_3C-$) and carboxylic ester (for example, the benzoyloxy group $PhC(O)O-$ and the acetyloxy group $CH_3C(O)O-$) groups, halogen atoms, $Cl-CH_2-$, and $Q^1-O-CH_2-$ groups in which $Q^1$ is H, an alkyl group or an acyl group;
- groups having an optionally substituted ethylenic unsaturation [originating, for example, from a vinyl unit ($CH=CH_2-$), an allyl unit ($CH_2=CH-CH_2-$) or an acryloyloxy unit ($CH_2=CH-C(O)-O-$)]; and
- amino groups $-N(Q^3)(Q^4)-$ in which $Q^3$ and $Q^4$ each represent, independently of one another, H, an alkyl group, an aryl group, an arylalkyl group or an acyl group, [for example $CH_3C(O)NH-$ or $PhCH_2NH-$].

An eighth family of sulfonylimides comprises the compounds (Ih) that correspond to the formula (I) in which Ar represents a heterocyclic aromatic group, in particular a pyridine group.

The N-benzylsulfimides and N-allylsulfimides obtained as intermediate products constitute another subject of the present invention. They correspond to the formula $RSO_2N(R'')SO_2R'$ (II) in which R has the more general meaning given previously, R" is a benzyl or allyl group, and R' is a linear or branched perfluoroalkyl group, preferably a $CF_3$ or $C_2F_5$ group.

A sulfonyl fluoride (III) is obtained by a method comprising a step of preparing a sulfinate $[Ar-Z-(CF_2)_n-CFR_f-SO_2]_mM$ (IV), and a step of converting the sulfinate to sulfonyl fluoride (III), Ar, Z and n having the preceding meaning, M' being an alkali metal or ammonium cation.

The methods of carrying out the step of preparing the sulfinate depend on the desired sulfinate, and especially on the nature of Z of the Ar—Z group that it contains.

An $Ar-S-(CF_2)_n-CFR_f-SO_2M$ sulfinate (denoted hereinafter by $IV_S$) in which Ar, $-(CF_2)_n-CFR_f-$ and M have the meaning given above may be obtained by a method comprising:
- a first step consisting in reducing a halide $Ar-S-(CF_2)_n-CFR_f-X$ in which X represents Br or Cl, via an excess of magnesium in the presence of trimethylsilyl chloride (TMSCl) to obtain a compound $Ar-S-(CF_2)_n-CFR_f-Si-(CH_3)_3$; and
- a second step during which the compound $Ar-S-(CF_2)_n-CFR_f-Si-(CH_3)_3$ is reacted with a fluoride of the cation M in the presence of $SO_2$ to obtain the sulfinate.

The first step is preferably carried out in THF, and the second step preferably in MeCN.

A compound of the $Ar-S-(CF_2)_n-CFR_f-Br$ type may be obtained by the reaction of the thiol $Ar-SH$ with a dibromide $Br-(CF_2)_n-CFR_f-Br$ using the dibromide in excess.

An $Ar-SO-(CF_2)_n-CFR_f-SO_2M$ sulfinate (denoted hereinafter by $IV_{SO}$) or an $Ar-SO_2-(CF_2)_n-CFR_f-SO_2M$ sulfinate (denoted hereinafter by $IV_{SO2}$) may be obtained by a method comprising:
- a first step consisting in reducing a halide $Ar-S-(CF_2)_n-CFR_f-X$ in which X represents F, Br or Cl, via an excess of magnesium in the presence of trimethylsilyl chloride (TMSCl) to obtain a compound $Ar-S-(CF_2)_n-CFR_f-Si-(CH_3)_3$;
- a second step during which the compound $Ar-S-(CF_2)_n-CFR_f-Si-(CH_3)_3$ is oxidized using metachloroperbenzoic acid (m-CPBA) in excess, the amount of acid being chosen as a function of the degree of oxidation [(IV) or (VI)] that it is desired to achieve for the S atom, the oxidation being advantageously carried out in anhydrous dichloromethane;
- a third step during which the silane obtained at the end of the second step is condensed with the sulfur dioxide in the presence of MF.

The methods of carrying out the step of obtaining a sulfonyl fluoride from a sulfinate depend on the desired sulfonyl fluoride, in particular on the nature of Z of the Ar—Z group that it contains in the general formula III.

A sulfonyl fluoride III may be obtained by reaction of the corresponding sulfinate IV with a fluorinating agent chosen from fluorine, xenon difluoride, potassium fluorosulfate, N-fluorobenzenesulfonimide, N-fluoro-pyridinium heptadiborate, N-fluoropyridinium trifluoro-methanesulfonate, N,N'-difluoro-2,2'-bipyridinium bis-(tetrafluoroborate) and 1-chloromethyl-4-fluoro-1,4-diazoniabicyclo[2.2.2]octane bis(tetrafluoroborate) (F-TEDA). The reaction may be carried out using sulfinate in solution in the solvent in which it was obtained, if said solvent is acetonitrile.

The fluorinating agents used for the fluorination of the sulfinate are commercially available products. For example, 1-chloromethyl-4-fluoro-1,4-diazoniabicyclo-[2.2.2]octane bis(tetrafluoroborate) (F-TEDA) corresponding to the formula

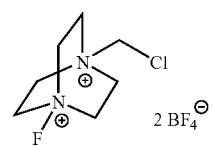

is sold under the name Selectfluor© by Air Products. Fluorine $F_2$, xenon difluoride $XeF_2$, potassium fluorosulfate $KSO_4F$, N-fluorobenzenesulfonimide $(PhSO_2)_2NF$, N-fluoropyridinium heptafluorodiborate

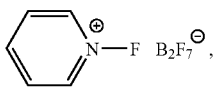

N-fluoropyridinium trifluoromethanesulfonate

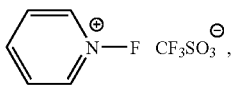

and N,N'-difluoro-2,2'-bipyridinium bis(tetrafluoroborate)

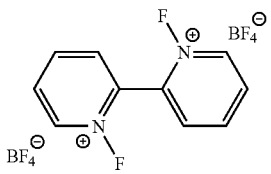

are sold, in particular, by Acros and Aldrich.

Said method may be advantageously carried out to obtain the following sulfonyl fluorides:

$$Ar-S-(CF_2)_n-CFR_f-SO_2F \qquad (III_S);$$

$$Ar-SO-(CF_2)_n-CFR_f-SO_2F \qquad (III_{SO});$$

$$Ar-SO_2-(CF_2)_n-CFR_f-SO_2F \qquad (III_{SO2}).$$

The sulfonyl fluorides $III_{SO}$ and $III_{SO2}$ may be obtained by oxidation of the corresponding fluoride $I_S$. The oxidation is advantageously carried out using meta-chloroperbenzoic acid (m-CPBA) in excess, the amount of acid being chosen as a function of the degree of oxidation (IV) or (VI) that it is desired to achieve for the S atom.

Generally, when an initial halide $Ar-S(CF_2)_n-CFR^f-X$ is not available for a particular Ar group, the Ar' group of an existing halide may be modified on the compound $Ar'-S-(CF_2)_n-CFR^f-Si(CH_3)_3$ (III), on the sulfinate $[Ar'-S-(CF_2)_n-CFR^f-SO_2]_mM$ (II) or on the sulfonyl fluoride $Ar'-S-(CF_2)_n-CFR^f-SO_2F$ (I).

The following table gives some examples of useful reactions, of which the implementation and the generalization are within the scope of a person skilled in the art.

| Ar' | Ar | Reaction |
|---|---|---|
| Br-Ph | (CH$_3$)$_3$Si-Ph | Reaction of a compound IV (Ar' is Br-Ph and X is Br) with Mg and TMSCl |
| CH$_3$OH-Ph | HO-Ph | Reaction of a compound I (Ar' is CH$_3$OH-Ph) with BBr$_3$, then NH$_4$OH |
| HO-Ph | CH$_2$=CH—C(O)—O-Ph | Reaction of a compound I (Ar' is HO-Ph) with acryloyl chloride and diisopropylethylamine |
| (CH$_3$)$_3$Si-Ph | I-Ph | Reaction of a compound III (Ar' is (CH$_3$)$_3$Si-Ph) with ICl |
| I-Ph | CH$_2$=CH-Ph | Reaction of a compound III (Ar' is I-Ph) with vinylmagnesium bromide in the presence of PdCl$_2$(PPh$_3$)$_2$ |
| F-Ph | RO-Ph | Reaction of a compound I (Ar' is F-Ph and Z = SO$_2$) with an alcoholate |
| F-Ph | Amino-Ph | Reaction of a compound I (Ar is F-Ph and Z = SO$_2$) with an amide or a compound that releases an amide, for example dimethylformamide |

The sulfonylimides (I) of the present invention may be incorporated into the composition of electrolytes that can be used in various electrochemical devices.

The sulfonylimides $I_{Li}$ are particularly useful as salts for the electrolyte of electrochemical devices such as non-rechargeable lithium cells, lithium polymer batteries, lithium ion batteries, organic supercapacitors and electrochromic devices.

In lithium cells, lithium ion batteries and organic supercapacitors, the electrolyte may be a liquid electrolyte containing the salt $I_{Li}$ in solution in a polar aprotic solvent. The aprotic liquid solvent, used alone or as a mixture, is chosen for example from linear ethers and cyclic ethers, esters, nitriles, nitrogen-containing derivatives, amides, sulfones, sulfolanes, alkylsulfamides and linear and cyclic carbonates. Particularly preferred solvents are diethyl ether, dimethoxyethane, glyme, tetrahydrofuran, dioxane, dimethyltetrahydrofuran, methyl or ethyl formate, propylene or ethylene carbonate, alkyl carbonates (especially dimethyl carbonate, diethyl carbonate and methylpropyl carbonate), butyrolactones, acetonitrile, benzonitrile, nitromethane, nitrobenzene, dimethylformamide, diethylformamide, N-methyl-pyrrolidone, dimethylsulfone, tetramethylenesulfone and tetraalkylsulfonamides having from 5 to 10 carbon atoms.

In one embodiment, the liquid electrolyte is used with a microporous or macroporous separator, the porosity of which it fills. The separator may be of PVDF, polysulfone, polyimide, Celgard® or Gore® fabric type.

In another embodiment, the liquid electrolyte is used to swell a non-porous polymer, thus forming a plasticized polymer electrolyte. The plasticized polymer electrolyte contains at least 80% by weight of liquid electrolyte and at most 20% by weight of polymer. For plasticized polymer electrolytes use is preferably made of a three-dimensional polymer based, for example, on polyoxyethylene, PVDF/HFP, polyacrylonitrile, polymethacrylate, polyacrylate, polymethacrylonitrile or on semi-interpenetrated networks of said polymers.

The sulfonylimides of organic cations, and more particularly the sulfonylimides of ammonium $I_{amm}$, of the present invention are particularly useful as ionic liquids in various electrochemical devices, especially non-rechargeable lithium cells, lithium ion batteries, organic supercapacitors and electrochromic devices.

The sulfonylimides $I_{amm}$ constitute ionic liquids that may advantageously replace an organic liquid solvent or mixture of organic liquid solvents.

In one embodiment, the compounds $I_{amm}$ are used in the pure state as ionic liquids in an electrochemical device such as an organic supercapacitor, in particular with a microporous or macroporous separator mentioned previously.

In a second embodiment, the compounds $I_{amm}$ are used in solution in an aprotic liquid solvent such as defined above, to form a liquid electrolyte that can be used in particular in an organic supercapacitor, in particular with a microporous or macroporous separator of PVDF, polysulfone, polyimide, Celgard® or Gore® fabric type.

In a third embodiment, the compounds $I_{amm}$ are dissolved in a dense polymer membrane optionally swollen by an organic solvent. Said polymer may be a functional polymer capable of absorbing large amounts of $I_{amm}$ compounds. For the swollen dense polymer electrolytes, use is preferably made of a three-dimensional polymer based, for example, on polyoxyethylene, on PVDF-HFP, on polyacrylonitrile, on polymethacrylate, on polyacrylate, on polymethacrylonitrile, or on semi-interpenetrated networks of said polymers or a functionalized polymer having a high $T_g$ such as functionalized polyethersulfones. When a polymer is plasticized by a liquid electrolyte based on ionic liquids of $I_{amm}$ type, the plasticized polymer electrolyte contains at least 60% by weight of liquid electrolyte and at most 40% by weight of polymer.

The ionic liquids $I_{amm}$ may be used as a mixture with a lithium salt (for example an $I_{Li}$ compound) in lithium cells, lithium ion batteries or organic supercapacitors. It is possible, if necessary, in order to reduce the viscosity, to add a polar aprotic solvent as defined above. The salt solutions in an ionic liquid are advantageously used with a microporous or macroporous separator, as defined above.

For the plasticized polymer electrolytes, use is preferably made of a three-dimensional polymer based, for example, on polyoxyethylene, on PVDF/HFP, on poly-acrylonitrile, on polymethacrylate, on polyacrylate, on polymethacrylonitrile or on semi-interpenetrated networks of said polymers.

A compound according to the present invention may be used in the form of a polymer electrolyte comprising the sulfonylimide $I_{Li}$ in solution in a solvating polymer that may or may not be plasticized by a polar liquid solvent or an ionic liquid $1_{amm}$.

The polymer solvent may be chosen from crosslinked or uncrosslinked solvating polymers, that may or may not bear grafted ionic groups. A solvating polymer is a polymer that comprises solvating units containing at least one heteroatom chosen from sulfur, oxygen or nitrogen. By way of example of solvating polymers, mention may be made of polyethers having a linear, comb or block structure, that may or may not form a network, based on polyoxyethylene or copolymers containing the ethylene oxide or propylene oxide or allyl glycidyl ether unit, polyphosphazenes and polysiloxanes having oligo(oxyethylene) side chains, crosslinked networks based on polyethylene glycol crosslinked by isocyanates or the networks obtained by polycondensation and bearing groups that allow the incorporation of crosslinkable groups. Mention may also be made of block copolymers in which certain blocks bear functions that have redox properties. Of course, the above list is not limiting and any polymers having solvating properties may be used.

When the solvent of the electrolyte is a plasticized solvating polymer, it contains at least 80% of polymer and at most 20% of polar liquid or of ionic liquid $I_{amm}$.

A lithium polymer battery comprises a negative electrode and a positive electrode separated by a solid polymer electrolyte. The positive electrode of a lithium polymer battery is constituted by a positive electrode active material, optionally a binder and a material that confers electronic conduction. In a rechargeable lithium battery, the anode is constituted by a film of metallic lithium, of a lithium alloy or of an intermetallic lithium compound. In a lithium ion type battery the negative electrode is constituted by a material capable of reversibly inserting lithium ions such as graphite for example. The sulfonylimide according to the invention used for the electrolyte may be a sulfonylimide $I_{li}$ or a sulfonylimide $I_{li}$ mixed with a sulfonylimide $I_{amm}$. Lithium salts of $A^-$, $Li^+$ type may be added to these sulfonylimides. The desired property is then to combine the high cation transport number of sulfonylimides $I_{li}$ with the high conductivities of other salts. Among the anions, mention may be made, non-exhaustively, of $ClO_4^-$, $BF_4^-$, $PF_6^-$, $AsF_6^-$, $(CF_3SO_2)_2N^-$, $(CF_3SO_2)_2CH^-$ and $(CF_3SO_2)_3C^-$.

The polymer electrolyte may be reinforced by addition of reinforcing fillers such as cellulose microfibrils.

In Ca batteries or Mg batteries a sulfonylimide $I_{ca}$ or $I_{mg}$ as defined above is used for the electrolyte. The negative electrode is constituted by the metal Ca or Mg and according to Novak et al., JPS, 1995, it is possible to use vanadates of $Mg(V_3O_8)$ type.

In a proton battery, the electrolyte advantageously contains a sulfonylimide $I_{ah}$.

A supercapacitor is constituted by an electrochemical cell comprising two electrodes separated by an electrolyte, in which the material constituting the electrodes has a very large specific surface area (for example from 100 to 1500 m$^2$/g). When the electrolyte of a supercapacitor comprises a sulfonylimide according to the present invention, said sulfonylimide is preferably chosen from the compounds $I_{amm}$ or $I_{Li}$ for organic supercapacitors or $I_{ah}$ for aqueous supercapacitors.

A fuel cell is an electrochemical device constituted by an anode and a cathode separated by an electrolyte. PEMFC (Proton Exchange Membrane Fuel Cell) fuel cells are membrane fuel cells that use hydrogen stored in a cylinder or hydrogen resulting from methanol reforming. DMFC (Direct Methanol Fuel Cell) fuel cells use methanol in the electrolyte solution. The use of PEMFCs is limited to temperatures less than or equal to 85° C. At higher temperature, the water evaporates and the conductivity of the ionomers decreases. It is therefore advantageous to find anhydrous proton conductors capable of operating beyond 130° C. The compounds II, are sufficiently conductive in the pure state. They may be used as a mixture with an excess of acid or of amine having been used to prepare them or (and) in the presence of $I_{amm}$. If their viscosities are too high they may be mixed with polar organic solvents such as sulfolane or tetraethylsulfonamide. To ensure the mechanical strength, the electrolyte may be used with a microporous or macroporous separator as defined previously, the porosity of which it impregnates. In another embodiment, the electrolyte is a membrane of a non-porous polymer swollen by $I_{ah}$. The choice of a functional polymer is essential to optimize the intake of $I_{ah}$ into the membrane. The functional polymer may be a non-ionic polymer or an ionomer such as Nafion or sulfonated polyethersulfones.

Electrochromic glazing is an electrochemical cell comprising two electrodes separated by an electrolyte. One of the electrodes is a transparent electrode, the other electrode may be constituted, for example, by a tungsten oxide WO$_3$ deposited on a film of tin oxide ITO. Under the action of a current, the color of the electrode WO$_3$ is modulated and changes from colorless to dark blue by insertion of protons. For this particular application a sulfonylimide $I_{ah}$ is preferably used.

BRIEF DESCRIPTION OF THE DRAWINGS

FIG. 1 is a table illustrating the results obtained for the electrolytes prepared from Example 23 with the PhSCF$_2$SO$_2$NSO$_2$CF$_3$Li salt.

DETAILED DESCRIPTION

Figure 1:
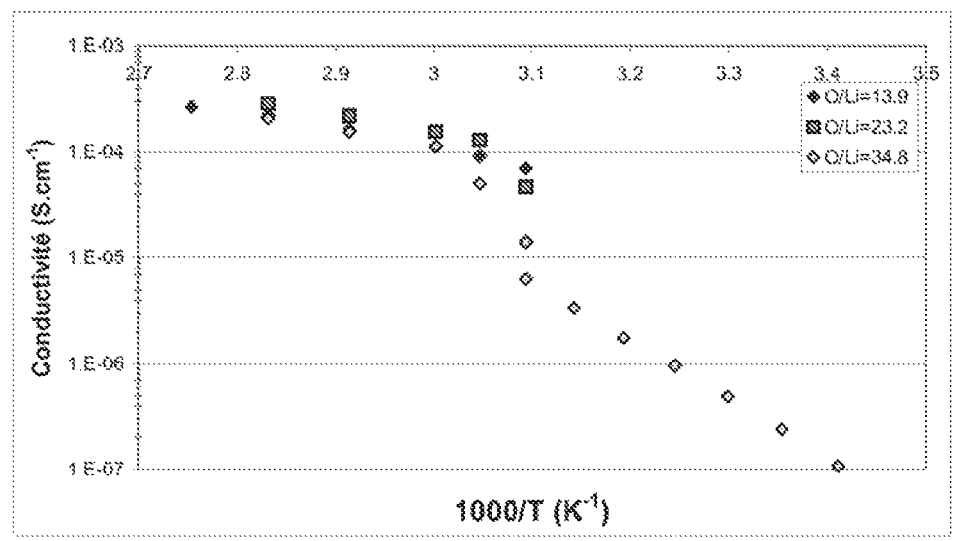
FIG. 1 is

The present invention is illustrated by the concrete examples described below, to which it is not however limited.

Example 1

[(2-Bromo-1,1,2,2-tetrafluoroethyl)sulfanyl]benzene

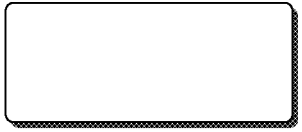

M = 289.09 g · mol$^{-1}$

In a three-necked round-bottomed flask placed under nitrogen, topped with a dry-ice condenser and a dropping funnel, thiophenol (10.2 ml, 100 mmol) was added dropwise (30 min) at 0° C. to a suspension of NaH (6 g, 150 mmol) in anhydrous DMF (100 ml). The mixture was then stirred at this temperature for 20 min then cooled to −50° C. 1,2-dibromo-1,1,2,2-tetrafluoroethane (15 ml, 125 mmol) was then added dropwise at −50° C. over 10 min. The mixture was then stirred for 2 h at this temperature, then 1 h at ambient temperature. Water (150 ml) was added to the reaction mixture, then the product was extracted with ethyl ether (3×100 ml). The organic phases were washed with water (3×100 ml) and dried over MgSO$_4$. After evaporation of the solvent, the residue was purified by distillation under reduced pressure (99° C./40 mmHg). The product [(2-bromo-1,1,2,2-tetrafluoroethyl)sulfanyl]benzene was then obtained in the form of a colorless liquid (26.07 g, 90%).

TLC: R$^f$ 0.8 (pentane)

$^{19}$F NMR (282 MHz, CDCl$_3$): δ −62.61 (t, 2F, C$\underline{F}_2$Br, $^3J_{F-F}$=8.0 Hz), −85.57 (t, 2F, SC$\underline{F}_2$, $^3J_{F-F}$=8.0 Hz).

$^1$H NMR (300 MHz, CDCl$_3$): δ 7.38-7.44 (m, 2H, H$_2$), 7.47-7.52 (m, 1H, H$_1$), 7.64-7.66 (d, 2H, H$_3$ $^3J_{H2-H3}$=7.1 Hz).

$^{13}$C NMR (75 MHz, CDCl$_3$): δ 116.93 (tt, 1C, CF$_2$ $^1J_{F-C}$=312.9 Hz, $^2J_{F-C}$=40.6 Hz), 122.78 (tt, 1C, CF$_2$, $^1J_{F-C}$=290.7 Hz, $^2J_{F-C}$=33.8 Hz), 123.6 (t, 1C, C$_{Ar\,4}$, $^3J_{F-C}$=2.7 Hz), 129.53 (s, 2C, C$_{Ar\,2}$), 131.09 (s, 1C, C$_{Ar\,1}$), 137.42 (s, 2C, C$_{Ar\,3}$).

The carbons CAr 1, CAr 2 and CAr 3 were determined on 2D NMR spectra by analogy with products from the same family.

Example 2

[(2-Phenylsulfanyl)-1,1,2,2-tetrafluoroethyl]trimethylsilane

M = 282.37 g · mol$^{-1}$

Under an inert atmosphere, PhSCF$_2$CF$_2$Br (3.7 g, 12.8 mmol) prepared according to the procedure from example 1 was added dropwise to a suspension of magnesium turnings (615 mg, 25.6 mmol), trimethylsilyl chloride (6.5 ml, 61 mmol) and anhydrous THF (25 ml), cooled to −20° C. The mixture was stirred at −20° C. for 1 h, then at ambient temperature for 5 h, then concentrated. The resulting solid was washed with pentane and the filtrate was evaporated to give [(2-phenylsulfanyl)-1,1,2,2-tezrafluoroethyl]trimethyl-silane in the form of a yellow liquid (3.3 g, 90%).

TLC: R$^f$ 0.7 (pentane)

$^{19}$F NMR (282 MHz, CDCl$_3$): δ −82.88 (t, 2F, SC$\underline{F}_2$, $^3J_{F-F}$=4.6 Hz), −122.56 (t, 2F, C$\underline{F}_2$Si, $^3J_{F-F}$=4.6 Hz).

$^1$H NMR (300 MHz, CDCl$_3$): δ 0.27 (s, 9H, Si(C$\underline{H}_3$)$_3$), 7.36-7.48 (m, 3H, H$_2$ and H$_1$), 7.64-7.66 (m, 2H, H$_3$).

$^{13}$C NMR (75 MHz, CDCl$_3$): δ −3.98 (m, 3C, Si(C$\underline{H}_3$)$_3$), 123.01 (tt, 1C, CF$_2$, $^1J_{F-C}$=273.2 Hz, $^3J_{F-C}$=45.3 Hz), 124.63 (m, 1C, C$_{Ar\,4}$), 127.54 (tt, 1C, CF$_2$, $^1J_{F-C}$=281.8 Hz, $^3J_{F-C}$=32.5 Hz), 129.21 (s, 2C, C$_{Ar\,2}$), 130.29 (s, 1C, C$_{Ar\,1}$), 137.31 (s, 2C, C$_{Ar\,3}$).

(Carbon not attributed precisely, but by analogy with products from the same family.)

Example 3

2-(Phenylsulfanyl)-1,1,2,2-tetrafluoroethylsulfonyl fluoride

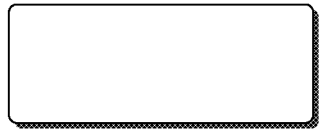

M = 292.25 g · mol$^{-1}$

A solution of sulfur dioxide was prepared by bubbling sulfur dioxide (1.02 g, 16 mmol) in a solution of anhydrous acetonitrile (20 ml) at ambient temperature. This solution was added to PhSCF$_2$CF$_2$SiMe$_3$ (8 mmol, prepared according to the procedure from example 2) and stirred at ambient temperature under an inert atmosphere. Anhydrous CsF (1.4 g, 9 mmol) was then added to the reaction mixture, which was stirred at ambient temperature overnight. The reaction was monitored by TLC and by 19$^F$ NMR (CDCl$_3$) until the disappearance of PhSCF$_2$CF$_2$SiMe$_3$. F-TEDA (2.9 g, 8.2 mmol) was added to the mixture, which was stirred for 1 h at ambient temperature. The mixture was concentrated and the solid residue washed with ethyl ether (10×50 ml). The filtrate was evaporated and the product purified by bulb-to-bulb distillation. The product 2-(phenylsulfanyl)-1,1,2,2-tetrafluoroethane-sulfonyl fluoride was obtained in the form of a colorless liquid (1.86 g, 79%).

TLC: R$^f$ 0.7 (pentane)

$^{19}$F NMR (282 MHz, CDCl$_3$): δ 45.93-46.02 (m, 1F, SO$_2$F), −86.52-86.59 (m, 2F, SC$\underline{F}_2$), −105.567 (m, 2F, C$\underline{F}_2$SO$_2$F).

$^1$H NMR (300 MHz, CDCl$_3$): δ 7.44 (dd, 2H, H$_2$, $^3J_{H2-H3}$=$^3J_{H2-H1}$=7.4 Hz), 7.54 (t, 1H, H$_1$, $^3J_{H1-H2}$=7.4 Hz), 7.67 (d, 2H, H$_3$, $^3J_{H2-H3}$=7.4 Hz).

$^{13}$C NMR (75 MHz, CDCl$_3$): δ 116.15 (ttd, 1C, C$_6$, $^1J_{F-C}$=300.6 Hz, $^2J_{F-C}$=40.8 Hz, $^2J_{F-C}$=32.6 Hz), 121.78 (ttd, 1C, C$_5$, $^1J_{F-C}$=290.9 Hz, $^2J_{F-C}$=31.7 Hz, $^3J_{F-C}$=1.2 Hz), 122.01 (t, 1C, C$_{Ar\,4}$, $^3J_{F-C}$=3.6 Hz), 129.80 (s, 2C, C$_{Ar\,2}$), 131.68 (s, 1C, C$_{Ar\,1}$), 137.53 (s, 2C, C$_{Ar\,3}$).

CAr 1, CAr 2 and CAr 3 were determined by 2D NMR.

Example 4

2-(Phenylsulfonyl)-1,1,2,2-tetrafluoroethanesulfonyl fluoride

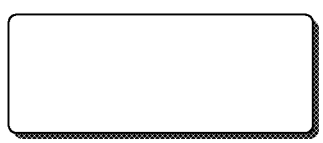

M = 324.24 g · mol$^{-1}$

Added to a solution of PhSCF$_2$CF$_2$SO$_2$F (1.32 g, 4.5 mmol, obtained according to the procedure from example 3) in anhydrous dichloromethane (45 ml) was metachloroperbenzoic acid (6.25 g, 36 mmol). The reaction medium was stirred at ambient temperature for 2 days (monitored by $^{19}$F NMR), then filtered over silica gel and washed with CH$_2$Cl$_2$. After evaporation of the solvent, the residue was purified by chromatography over silica gel (pentane/CH$_2$Cl$_2$, 4/1). The product 2-(phenylsulfonyl)-1,1,2,2-tetrafluoroethanesulfonyl fluoride was obtained in the form of a colorless liquid (1.15 g, 79%).

TLC: R$^f$ 0.7 (pentane/CH$_2$Cl$_2$, 1/1)

$^{19}$F NMR (282 MHz, CDCl$_3$): δ 46.20-46.30 (m, 1F, SO$_2$F), −106.27; −106.37 (m, 2F), −110.72; −110.83 (m, 2F).

$^1$H NMR (300 MHz, CDCl$_3$): δ 7.71 (dd, 2H, H$_2$, $^3J_{H2-H3}$=$^3J_{H2-H1}$=7.5 Hz), 7.89 (t, 1H, H$_1$, $^3J_{H1-H2}$=7.5 Hz), 8.06 (d, 2H, H$_3$, $^3J_{H2-H3}$=7.5 Hz).

$^{13}$C NMR (75 MHz, CDCl$_3$): δ 113.55 (tt, 1C, C$_5$, $^1J_{F-C}$=302.0 Hz, $^3J_{F-C}$=35.0 Hz), 115.41 (ttd, 1C, C$_6$, $^1J_{F-C}$=302.0 Hz, $^3J_{F-C}$=35.0 Hz, $^3J_{F-C}$=35.0 Hz), 130.14 (s, 2C, C$_{Ar\ 2}$), 131.35 (s, 2C, C$_{Ar\ 3}$), 131.77 (s, 1C, C$_{Ar\ 4}$), 137.20 (s, 1C, C$_{Ar\ 1}$).

Example 5

[(Bromodifluoromethyl)sulfanyl]benzene

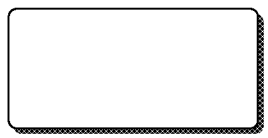

M = 239.08 g · mol$^{-1}$

In a three-necked round-bottomed flask placed under a nitrogen atmosphere, topped with a dry-ice condenser and a dropping funnel, thiophenol (10.2 ml, 100 mmol) was added dropwise, over 40 min at 0° C., to a suspension of NaH (6 g, 150 mmol) in anhydrous DMF (100 ml). The mixture was then stirred at 0° C. for 30 min then cooled to −50° C. Dibromodifluoromethane (27 ml, 300 mmol) was then added at −50° C. The mixture was then stirred for 3 h at this temperature, then 30 min at ambient temperature. Water (100 ml) was added to the reaction mixture, then the product was extracted with ethyl ether (3×100 ml). The organic phases were washed with water (3×100 ml) and dried over MgSO$_4$. After evaporation of the solvent, the residue was purified by distillation under reduced pressure (97° C./34 mmHg) to give the product [(bromodifluoromethyl)sulfanyl]benzene in the form of a colorless liquid (15.3 g, 60%).

TLC: R$^f$ 0.7 (pentane)

$^{19}$F NMR (282 MHz, CDCl$_3$): δ −22.53 (s, 2F).

$^1$H NMR (300 MHz, CDCl$_3$): δ 7.43 (m, 2H, H$_2$), 7.52 (m, 1H, H$_1$), 7.66 (d, 2H, H$_3$, $^3J_{H2-H3}$=7.4 Hz).

$^{13}$C NMR (75 MHz, CDCl$_3$): δ 119.41 (t, 1C, CF$_2$, $^1J_{F-C}$=336.0 Hz), 127.30 (t, 1C, C$_{Ar\ 4}$, $^3J_{F-C}$=1.1 Hz), 129.58 (s, 2C, C$_{Ar\ 2}$), 131.18 (s; 1C, C$_{Ar\ 1}$), 136.52 (s, 2C, C$_{Ar\ 3}$).

Example 6

[Difluoro(phenylsulfanyl)methyl]trimethylsilane

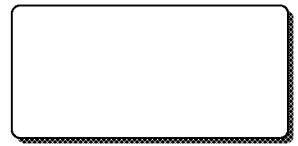

M = 232.37 g · mol$^{-1}$

Under an inert atmosphere, PhSCF$_2$Br (4.8 g, 20 mmol, obtained according to the procedure from example 5) was added dropwise to a suspension of magnesium turnings (960 mg, 40 mmol), trimethylsilyl chloride (10.2 ml, 80 mmol) and anhydrous THF (50 ml) cooled to 0° C. The mixture was then stirred at 00° C. for 1 h, then at ambient temperature for 1 h. The mixture was then concentrated and the resulting solid was washed with petroleum ether. The organic phase was evaporated under vacuum to give the product [difluoro(phenylsulfanyl)-methyl]trimethylsilane in the form of a yellow liquid (4.3 g, 92%).

TLC: R$_f$ 0.5 (pentane)

$^{19}$F NMR (282 MHz, CDCl$_3$): δ −88.01 (s, 2F).

$^1$H NMR (300 MHz, CDCl$_3$): δ 0.25 (s, 9H, Si(CH$_3$)$_3$), 7.35-7.40 (m, 3H, H$_2$ and H$_1$), 7.58-7.61 (m, 2H, H$_3$).

$^{13}$C NMR (75 MHz, CDCl$_3$): δ −4.08 (t, 3C, Si(CH$_3$)$_3$, $^3J_{F-C}$=1.3 Hz, 126.44 (t, 1C, C$_{Ar\ 4}$), $^3J_{F-C}$=4.1 Hz), 128.93 (s, 2C, C$_{Ar\ 2}$), 129.40 (s, 1C, C$_{Ar\ 1}$), 134.10 (t, 1C, CF$_2$, $^1J_{F-C}$=300.2 Hz), 136.30 (t, 2C, C$_{Ar\ 3}$, $^4J_{F-C}$=1.1 Hz).

Example 7

Difluoro(phenylsulfanyl)methanesulfonyl fluoride

M = 242.24 g · mol$^{-1}$

A solution of sulfur dioxide was prepared by bubbling sulfur dioxide (3.9 g, 61 mmol) in a solution of anhydrous acetonitrile (20 ml) at ambient temperature. This solution was added to PhSCF$_2$SiMe$_3$ (4.3 g, 18.4 mmol, obtained according to the procedure from example 6) and stirred at ambient temperature under an inert atmosphere. Anhydrous CsF (2.8 g, 18.5 mmol) was then added to the reaction mixture, which was stirred at ambient temperature overnight. The reaction was monitored by TLC and by $^{19}$F NMR (CDCl$_3$) until the disappearance of PhSCF$_2$SiMe$_3$. F-TEDA (7.15 g, 20 mmol) was added to the mixture, at −20° C., which was then stirred for 1 h at ambient temperature. The mixture was concentrated and the solid residue washed with ethyl ether (10×50 ml). The filtrate was evaporated and the product purified by bulb-to-bulb distillation. The product difluoro(phenylsulfanyl)methanesulfonyl fluoride was obtained in the form of a colorless liquid (2.5 g, 57%).

TLC: R$_f$ 0.6 (pentane)

$^{19}$F NMR (282 MHz, CDCl$_3$): δ 35.06 (t, 1F, SO$_2$F, $^3J_{F-F}$=4.6 Hz), −76.08 (d, 2F, —SCF$_2$—, $^3J_{F-F}$=4.6 Hz).

$^1$H NMR (300 MHz, CDCl$_3$): δ 7.46 (dd, 2H, H$_2$, $^3J_{H2-H1}$=$^3J_{H2-H3}$=7.5 Hz), 7.56 (t, 1H, H$_1$, $^3J_{H1-H2}$=7.5 Hz), 7.71 (d, 2H, H$_3$, $^3J_{H3-H2}$=7.5 Hz).

$^{13}$C NMR (75 MHz, CDCl$_3$): δ 121.83 (t, 1C, C$_{Ar\ 4}$, $^3J_{F-C}$=3.0 Hz), 126.56 (td, 1C, CF$_2$, $^1J_{F-C}$=323.3 Hz, $^2J_{F-C}$=32.9 Hz), 129.95 (s, 2C, C$_{Ar\ 2}$), 132.13 (s, 1C, C$_{Ar\ 1}$), 137.52 (t, 2C, C$_{Ar\ 3}$, $^4J_{F-C}$=1.1 Hz).

Example 8

N-benzyl-2-(phenylsulfanyl)-1,1,2,2-tetrafluoroethanesulfonamide

M = 379.39 g · mol$^{-1}$

Added to a solution of 1,2-dichloroethane (20 ml), containing the PhSCF$_2$CF$_2$SO$_2$F (2.09 g, 7.2 mmol) obtained according to the method from example 3, was freshly distilled benzylamine (4 ml, 37 mmol). The mixture was stirred and heated at 50° C. for 20 h until the disappearance of PhSCF$_2$CF$_2$SO$_2$F (monitored by TLC and $^{19}$F NMR/CDCl$_3$). After returning to ambient temperature, an aqueous solution of HCl (10%) was added to the reaction medium. The aqueous and organic phases were separated and the aqueous phase was extracted with dichloromethane. The organic phases were combined and dried over MgSO$_4$. After filtration and evaporation of the solvents, the residue was purified by chromatography over silica gel (pentane to pentane/AcOEt:4/1). The sulfonamide product was obtained in the form of a white solid (2.1 g, 77%).

TLC: R$_f$ 0.8 (pentane/AcOEt 4/1)

$^{19}$F NMR (282 MHz, CDCl$_3$): δ −85.29 (t, 2F, SCF$_2$, $^3J_{F-F}$=5.7 Hz), −109.84 (t, 2F, CF$_2$SO$_2$N, $^3J_{F-F}$=5.7 Hz).

$^1$H NMR (300 MHz, CDCl$_3$): δ 4.45 (d, 2H, H8, $^3J_{H7-H8}$=5.8 Hz), 5.05 (t, 1H, NH, $^3J_{H7-H8}$=5.8 Hz) 7.31-7.53 (m, 8H, H$_{Ar}$), 7.68 (d, 2H, H$_3$, $^3J_{H2-H3}$=7.2 Hz).

$^{13}$C NMR (75 MHz, CDCl$_3$): δ 48.52 (s, C8), 116.09 (tt, 1C, CF$_2$, $^1J_{F-C}$=294.2 Hz, $^2J_{F-C}$=36.8 Hz), 123.24 (tt, 1C, CF$_2$, $^1J_{F-C}$=290.3 Hz, $^2J_{F-C}$=32.3 Hz), 123.51 (t, 1C, C$_{Ar\ 4}$, $^3J_{F-C}$=2.7 Hz), 128.00 (s, C$_{Ar}$), 128.56 (s, C$_{Ar}$), 129.07 (s, C$_{Ar}$), 129.48 (s, C$_{Ar}$), 131.077 (s, C$_{Ar}$), 135.67 (s, C$_{Ar\ 9}$), 137.45 (s, 2C, C$_{Ar\ 3}$).

Example 9

N-benzyl-2-(phenylsulfanyl)-1,1,2,2-tetrafluoro-N-(trifluoromethylsulfonyl)ethanesulfonamide M = 511.45 g · mol$^{-1}$ Added to a solution of dichloromethane (10 ml) containing the PhSCF$_2$CF$_2$SO$_2$NHBn prepared according to example 8 (750 mg, 2 mmol) was DIEA (420 µl, 2.4 mmol). Triflic anhydride (CF$_3$SO$_2$)$_2$O (510 µl, 3 mmol) was then added to the mixture at 0° C., which was stirred for 30 min at this temperature, then 1 h at ambient temperature (monitored by $^{19}$F NMR/CDCl$_3$). An aqueous solution of HCl (3%) was added to the mixture, the aqueous and organic phases were separated and the aqueous phase was extracted with dichloromethane. The organic phases were combined and dried over MgSO$_4$ and the solvents were evaporated. The residue was dissolved in hot pentane and the supernatant was recovered. After evaporation of the solvent, the sulfonamide product was obtained in the form of a white solid (925 mg, 91%).

$^{19}$F NMR (282 MHz, CDCl$_3$): δ −72.82 (s, 3F, CF$_3$, −85.89 (broad s, 2F, SCF$_2$), −102.85 (broad s, 2F, CF$_2$SO$_2$N).

$^1$H NMR (300 MHz, CDCl$_3$): δ 5.07 (s, 2H, H8), 7.37-7.55 (m, 8H, H$_{Ar}$), 7.65 (d, 2H, H$_3$, $^3J_{H2-H3}$=7.4 Hz).

$^{13}$C NMR (75 MHz, CDCl$_3$): δ 56.56 (s, C8), 116.70 (tt, 1C, CF$_2$, $^1J_{F-C}$=305.2 Hz, $^2J_{F-C}$=39.0 Hz), 119.15 (q, 1C, C7, $^1J_{F-C}$=324.9 Hz), 122.50 (tt, 1C, CF$_2$, $^1J_{F-C}$=292.4 Hz, $^2J_{F-C}$=31.3 Hz), 122.89 (t, 1C, C$_{Ar4}$, $^3J_{F-C}$=3.3 Hz), 128.89 (s, C$_{Ar}$), 129.65 (s, C$_{Ar}$), 129.71 (s, C$_{Ar}$), 130.12 (s, C$_{Ar}$), 131.43 (s, C$_{Ar}$), 132.27 (s, C$_{Ar9}$), 137.52 (s, 2C, C$_{Ar3}$).

Example 10

Lithium 2-(phenylsulfanyl)-1,1,2,2-tetrafluoro-N-(trifluoromethylsulfonyl)ethanesulfonamide M = 427.27 g · mol$^{-1}$ A solution in ethanol (5 ml) of the compound prepared according to example 9 (510 mg, 1 mmol) was prepared. The mixture was stirred for 8 h at ambient temperature, then LiOH.H$_2$O (42 mg, 1 mmol) was added. The mixture was then stirred overnight, then evaporated to dryness. The residue was dissolved in diethyl ether then filtered. After evaporation of the filtrate and washing of the resulting solid with pentane, the lithium salt was obtained in the form of a white solid (385 mg, 90%).

$^{19}$F NMR (282 MHz, acetone D6): δ −80.29 (s, 3F, C$\underline{F}_3$), −84.94 (t, 2F, SC$\underline{F}_2$), $^3J_{F-F}$=5.7 Hz), −112.04 (t, 2F, C$\underline{F}_2$SO$_2$N, $^3J_{F-F}$=5.7 Hz).

$^1$H NMR (300 MHz, acetone D6): δ 7.46-7.58 (m, 3H, H$_{Ar}$), 7.67-7.70 (m, 2H, H$_3$).

$^{13}$C NMR (75 MHz, acetone D6): δ 115.06 (tt, 1C, CF$_2$, $^1J_{F-C}$=293.1 Hz, $^2J_{F-C}$=34.4 Hz), 120.59 (q, 1C, C7, $^1J_{F-C}$=321.5 Hz), 123.99 (tt, 1C, CF$_2$, $^1J_{F-C}$=290.4 Hz, $^2J_{F-C}$=32.5 Hz), 124.41 (m, 1C, C$_{Ar4}$), 130.19 (s, C$_{Ar}$), 131.59 (s, C$_{Ar}$), 137.86 (s, 2C, C$_{Ar3}$).

Example 11

Triethylammonium 2-(phenylsulfanyl)-1,1,2,2-tetrafluoro-N-(trifluoromethanesulfonyl)ethanesulfonamide M = 522.52 g · mol$^{-1}$ A solution in ethanol (4 ml) of the compound prepared according to example 9 (350 mg, 0.7 mmol) was prepared. The mixture was stirred for 8 h at ambient temperature, then triethylamine (100 μl, 0.7 mmol) was added. The mixture was then stirred overnight, then evaporated to dryness. The residue was washed with pentane (elimination of the supernatant). After drying under vacuum, the triethylammonium salt was obtained in the form of a yellow liquid (300 mg, 82%).

$^{19}$F NMR (282 MHz, CDCl$_3$): δ −79.39 (s, 3F), −84.97 (m, 2F, PhSC$\underline{F}_2$), −110.65 (m, 2F, CF$_2$C$\underline{F}_2$SO$_2$N).

$^1$H NMR (300 MHz, CDCl$_3$): δ 1.23 (t, 9H, H8, $^3J_{H8-H9}$=7.3 Hz), 3.07-3.14 (m, 6H, H9), 6.78 (broad s, 1H, NH), 7.34-7.47 (m, 3H, H$_{Ar}$), 7.62 (d, 2H, H3, $^3J_{H2-H3}$=7.2 Hz).

$^{13}$C NMR (75 MHz, CDCl$_3$): δ 114.65 (tt, $^1J_{F-C}$=294.2 Hz, $^2J_{C-F}$=35.9 Hz), 119.72 (q, C7, $^1J_{C-F}$=320.9 Hz), 123.26 (tt, $^1J_{C-F}$=290.0 Hz, $^2J_{C-F}$=32.0 Hz), 123.46 (t, C$_{Ar4}$, $^3J_{C-F}$=2.7 Hz), 129.31 (s, C$_{Ar2}$), 130.90 (s, C$_{Ar1}$), 137.24 (s, C$_{Ar3}$).

The triethylammonium salt obtained was dried under vacuum for 48 hours at 120° C. to eliminate any trace of water, then stored in a glovebox under argon. The viscous liquid obtained after this treatment was used to impregnate a macroporous separator made of polyethylene/polypropylene over 12 hours in a glovebox. Next, the impregnated separator was mounted in a conductivity measuring cell and measurements were carried out from 25 to 110° C. A conductivity of 1.8 mS/cm was obtained at 110° C. The measurement carried out on the pure salt, that is to say without a macroporous support, provided a value of 4.5 mS/cm at 110° C.

Example 12

Lithium 2-(phenylsulfanyl)-1,1,2,2-tetrafluoro-N-[2-(phenylsulfanyl)-1,1,2,2-tetrafluoroethanesulfonyl]-ethanesulfonamide M = 567.44 g · mol$^{-1}$ A 1M solution (1 ml, 1 mmol) of the lithiated derivative of hexamethyldisilazane in THF was added at −20° C. to the compound PhSCF$_2$CF$_2$SO$_2$F (584 mg, 2 mmol), the mixture was stirred at ambient temperature for 24 h, then heated at 70° C. for 6 days. The mixture was evaporated and the residual solid washed with pentane. The desired lithium salt was obtained in the form of a white solid (230 mg, 40%) contaminated by some fluorine-containing impurities.

$^{19}$F NMR (282 MHz, CDCl$_3$): δ −83.33 (t, 2F, SC$\underline{F}_2$, $^3J_{F-F}$=8.0 Hz), −112.78 (t, 2F, C$\underline{F}_2$SO$_2$N, $^3J_{F-F}$=8.0 Hz).

$^1$H NMR (300 MHz, CDCl$_3$): δ 7.43-7.55 (m, 3H, H$_1$ and H$_2$), 7.60-7.63 (m, 2H, H$_3$).

Example 13

N-benzyl-2-(phenylsulfonyl)-1,1,2,2-tetrafluoroethanesulfonamide

M = 411.39 g · mol$^{-1}$

Added to a solution of 1,2-dichloroethane (5 ml), containing the PhSO$_2$CF$_2$CF$_2$SO$_2$F (325 mg, 1 mmol) prepared according to the method from example 4, was freshly distilled benzylamine (550 μl, 5 mmol). The mixture was stirred and heated at 50° C. for 20 h until the disappearance of PhSO$_2$CF$_2$CF$_2$SO$_2$F (monitored by TLC and $^{19}$F NMR/CDCl$_3$). After returning to ambient temperature, an aqueous solution of HCl (10%) was added to the reaction medium. The aqueous and organic phases were separated and the aqueous phase was extracted with dichloromethane. The organic phases were combined and dried over MgSO$_4$. After filtration and evaporation of the solvents, the residue was purified by chromatography over silica gel (pentane to pentane/AcOEt: 4/1). The sulfonamide product was obtained in the form of a white solid (340 mg, 83%).

$^{19}$F NMR (282 MHz, CDCl$_3$): δ −110.09 (m, 2F), −110.25 (m, 2F).

$^1$H NMR (300 MHz, CDCl$_3$): δ 4.47 (d, 2H, H8, $^3J_{H7\text{-}H8}$=5.7 Hz), 5.30 (t, 1H, NH, $^3J_{H7\text{-}H8}$=5.7 Hz), 7.30-7.39 (m, 5H, H$_{Ar}$), 7.65-7.70 (m, 2H, H$_2$), 7.81-7.87 (m, 1H, H$_1$), 8.04 (d, 2H, H$_3$, $^3J_{H2\text{-}H3}$=7.7 Hz).

Example 14

N-benzyl-2-(phenylsulfonyl)-1,1,2,2-tetrafluoro-N-(trifluoromethanesulfonyl)ethanesulfonamide

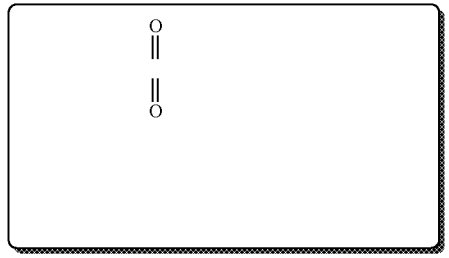

M = 543.45 g · mol$^{-1}$

Added to a solution of dichloromethane (5 ml) containing the PhSO$_2$CF$_2$CF$_2$SO$_2$NHBn (205 mg, 0.5 mmol) obtained according to the method from example 13, was DIEA (100 μl, 0.55 mmol). Triflic anhydride (150 μl, 0.85 mmol) was then added to the mixture at 0° C., which was stirred for 30 min at this temperature, then 1 h at ambient temperature (monitored by $^{19}$F NMR/CDCl$_3$). An aqueous solution of HCl (3%) was added to the mixture, the aqueous and organic phases were separated and the aqueous phase was extracted with dichloromethane. The organic phases were combined and dried over MgSO$_4$ and the solvents were evaporated. The residue was dissolved in hot pentane and the supernatant was recovered. After evaporation of the solvent, the sulfonimide product was obtained in the form of a white solid (120 mg, 44%).

$^{19}$F NMR (282 MHz, CDCl$_3$): δ −72.67 (s, 3F, CF$_3$), −103.30 (broad s, 2F), −110.23 (broad s, 2F).

$^1$H NMR (300 MHz, CDCl$_3$): δ 5.07 (s, 2H, H$_8$), 7.26-7.49 (m, 5H, H$_{Ar}$), 7.65 (dd, 2H, H$_2$, $^3J_{H1\text{-}H2}$=$^3J_{H2\text{-}H3}$=7.5 Hz), 7.85 (t, 1H, H$_1$, $^3J_{H1\text{-}H2}$=7.5 Hz), 8.01 (d, 2H, H$_3$, $^3J_{H2\text{-}H3}$=7.5 Hz).

Example 15

Lithium 2-(phenylsulfonyl)-1,1,2,2-tetrafluoro-N-(trifluoromethanesulfonyl)ethanesulfonamide

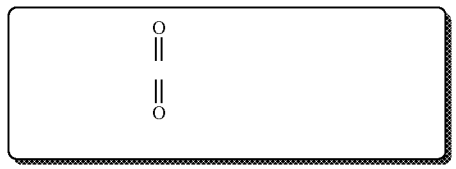

M = 459.26 g · mol$^{-1}$

A solution in ethanol (10 ml) of the compound prepared according to example 14 (800 mg, 1.5 mmol) was prepared. The mixture was stirred for 8 h at ambient temperature, then LiOH.H$_2$O (63 mg, 1 mmol) was added. The mixture was then stirred overnight, then evaporated to dryness. The residue was dissolved in diethyl ether then filtered. After evaporation of the filtrate and washing of the resulting solid with pentane, the lithium salt was obtained in the form of a white solid (400 mg, 59%).

$^{19}$F NMR (282 MHz, DMSO): δ −79.17 (s, 3F, CF$_3$), −110.49 (m, 2F), −111.75 (m, 2F).

$^1$H NMR (300 MHz, DMSO): δ 7.78-7.84 (m, 2H, H$_{Ar}$), 7.96-8.02 (m, 1H, H$_{Ar}$), 8.05-8.08 (m, 2H, H$_{Ar}$).

Example 16

N-benzyldifluoro(phenylsulfanyl)methanesulfonamide

M = 329.39 g · mol$^{-1}$

Added to a solution of 1,2-dichloroethane (15 ml), containing the PhSCF$_2$SO$_2$F (1.46 g, 5 mmol) obtained according to the method from example 7, was freshly distilled benzylamine (2.7 ml, 25 mmol). The mixture was stirred and heated at 50° C. for 20 h until the disappearance of PhSCF$_2$SO$_2$F (monitored by TLC and $^{19}$F NMR/CDCl$_3$). After returning to ambient temperature, an aqueous solution of HCl (10%) was added to the reaction medium. The aqueous and organic phases were separated and the aqueous phase was extracted with dichloromethane. The organic phases were combined and dried over MgSO$_4$. After filtration and evaporation of the solvents, the residue was purified by chromatography over silica gel (pentane to pentane/AcOEt:4/1). The sulfonamide product was obtained in the form of a white solid (1.5 g, 90%).

$^{19}$F NMR (282 MHz, CDCl$_3$): δ −77.99 (s, 2F).

$^1$H NMR (300 MHz, CDCl$_3$): δ 4.40 (d, 2H, H7, $^3J_{H6\text{-}H7}$=5.8 Hz), 4.94 (t, 1H, NH, $^3J_{H6\text{-}H7}$=5.8 Hz), 7.29-7.53 (m, 8H, H$_{Ar}$), 7.70 (d, 2H, H3, $^3J_{H2\text{-}H3}$=7.0 Hz).

$^{13}$C NMR (75 MHz, CDCl$_3$): δ 48.40 (s, C7), 123.77 (t, C$_{Ar4}$, $^3J_{C\text{-}F}$=2.7 Hz), 127.90 (s, C$_{Ar}$), 128.07 (t, C5, $^1J_{C-F}$=320.0 Hz), 128.35 (s, $C_{Ar}$), 128.95 (s, $C_{Ar}$), 129.46 (s, $C_{Ar}$), 131.01 (s, $C_{Ar}$), 136.06 (s, $C_{Ar8}$), 137.15 (t, $C_{Ar3}$, $^4J_{C-F}$=1.1 Hz).

Example 17

N-benzyldifluoro(phenylsulfanyl)-N-trifluoromethanesulfonylmethanesulfonamide

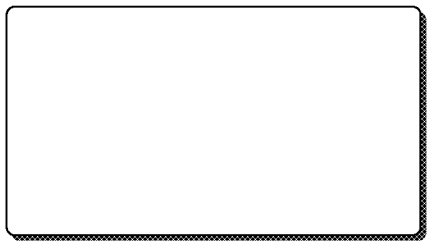

M = 461.45 g · mol$^{-1}$

Added to a solution of dichloromethane (10 ml) containing the PhSCF$_2$SO$_2$NHBn prepared according to example 16 (1.49 mg, 4.5 mmol) was DIEA (830 µl, 4.75 mmol). Triflic anhydride (CF$_3$SO$_2$)$_2$O (1.15 ml, 6.75 mmol) was then added to the mixture at 0° C., which was stirred for 30 min at this temperature, then 1 h at ambient temperature (monitored by $^{19}$F NMR/CDCl$_3$). An aqueous solution of HCl (3%) was added to the mixture, the aqueous and organic phases were separated and the aqueous phase was extracted with dichloromethane. The organic phases were combined and dried over MgSO$_4$ and the solvents were evaporated. The residue was dissolved in hot pentane and the supernatant was recovered. After evaporation of the solvent, the sulfonamide product was obtained in the form of a white solid (1.85 g, 89%).

$^{19}$F NMR (282 MHz, CDCl$_3$): δ −72.59 (s, 2F), −72.96 (s, 3F).

$^1$H NMR (300 MHz, CDCl$_3$): δ 5.03 (s, 2H, H7) 7.34-7.56 (m, 8H, H$_{Ar}$), 7.69 (d, 2H, H3, $^3J_{H2-H3}$=7.3 Hz).

$^{13}$C NMR (75 MHz, CDCl$_3$): δ 56.33 (s, C7), 118.99 (q, C6, $^1J_{C-F}$=324.9 Hz), 122.44 (t, $C_{Ar4}$, $^3J_{C-F}$=3.0 Hz), 128.77 (s, $C_{Ar}$), 128.87 (t, C5, $^1J_{C-F}$=327.9 Hz), 129.46 (s, $C_{Ar}$), 129.73 (s, $C_{Ar}$), 129.95 (s, $C_{Ar}$), 131.71 (s, $C_{Ar}$), 132.69 (s, $C_{Ar6}$), 137.42 (t, $C_{Ar3}$, $^4J_{C-F}$=1.1 Hz).

Example 18

Lithium difluorophenylsulfanyl-N-(trifluoromethanesulfonyl)methanesulfonamide

M = 377.26 g · mol$^{-1}$

A solution in ethanol (20 ml) of the compound prepared according to example 17 (1.38 g, 3 mmol) was prepared. The mixture was stirred for 8 h at ambient temperature, then LiOH.H$_2$O (125 mg, 3 mmol) was added. The mixture was then stirred overnight, then evaporated to dryness. The residue was dissolved in diethyl ether then filtered. After evaporation of the filtrate and washing of the resulting solid with pentane, the lithium salt was obtained in the form of a white solid (950 mg, 85%).

$^{19}$F NMR (282 MHz, acetone D6): δ −79.00 (s, 2F), −80.08 (s, 3F).

$^1$H NMR (300 MHz, acetone D6): δ 7.41-7.53 (m, 3H, H$_{Ar}$), 7.63-7.66 (m, 2H, H3).

$^{13}$C NMR (75 MHz, acetone D6): δ 120.95 (q, C6, $^1J_{C-F}$=321.8 Hz), 126.05 (m, $C_{Ar4}$), 128.72 (t, C5, $^1J_{C-F}$=319.4 Hz), 130.01 (s, $C_{Ar}$), 131.12 (s, $C_{Ar}$), 137.37 (s, $C_{Ar}$).

Example 19

N-benzyl(phenylsulfonyl)difluoromethanesulfonamide

N-benzyl(phenylsulfonyl)difluoromethanesulfonamide was prepared from difluoro(phenylsulfonyl)methanesulfonyl fluoride.

Preparation of difluoro(phenylsulfonyl)methanesulfonyl fluoride

Added to a solution of PhSCF$_2$SO$_2$F (2.23 g, 9.2 mmol), prepared according to the procedure described in example 7, in anhydrous dichloromethane (90 ml) was 12 g (70 mmol) of metachloroperbenzoic acid. The reaction medium was stirred at ambient temperature for 3 days (monitored by $^{19}$F NMR), then filtered over silica gel and washed with CH$_2$Cl$_2$. After evaporation of the solvent, the residue was purified by chromatography on silica gel (pentane/CH$_2$Cl$_2$, 4/1). The product difluoro(phenylsulfonyl)methanesulfonyl fluoride was obtained in the form of a colorless liquid.

TLC: R$_f$ 0.65 (pentane/CH$_2$Cl$_2$, 1/1)

$^{19}$F NMR (282 MHz, CDCl$_3$): δ 49.28 (t, 1F, SO$_2$F, $^3J_{F-F}$=5.7 Hz), −99.40 (d, 2F, CF$_2$, $^3J_{F-F}$=5.7 Hz).

$^1$H NMR (300 MHz, CDCl$_3$): δ 7.70 (t, 2H, H$_2$, $^3J_{H2-H3}$=$^3J_{H2-H1}$=7.6 Hz), 7.90 (t, 1H, H$_1$, $^3J_{H1-H2}$=7.6 Hz), 8.09 (d, 2H, H$_3$, $^3J_{H2-H3}$=7.6 Hz).

$^{13}$C NMR (75 MHz, CDCl$_3$): δ 118.76 (td, 1C, CF$_2$, $^1J_{F-C}$=336.3 Hz, $^3J_{F-C}$=30.0 Hz), 130.24 (s, 2C, $C_{Ar2}$), 130.99 (s, 1C, $C_{Ar4}$), 131.58 (s, 2C, $C_{Ar3}$), 137.66 (s, 1C, $C_{Ar1}$).

Preparation of N-benzyl(phenylsulfonyl)difluoromethane-sulfonamide

The following method was carried out. Added to a solution of sulfonyl fluoride (1.1 mmol) in anhydrous 1,2-dichloroethane (C≈0.2 M) was, under an inert atmosphere at −20° C., freshly distilled benzylamine (5.5 mmol). The mixture was stirred and slowly brought to ambient temperature over 20 h until the disappearance of the sulfonyl fluoride (monitored by TLC and $^{19}$F NMR/CDCl$_3$). After returning to ambient temperature, an aqueous solution of HCl (10%) was added to the reaction medium. The aqueous and organic phases were separated and the aqueous phase was extracted with dichloromethane. The organic phases were combined and dried over MgSO$_4$. After filtration and evaporation of the solvents, the residue was purified by chromatography on silica gel (pentane to pentane/AcOEt: 4/1). Thus, 0.30 g (0.83 mmol) of N-benzyl sulfonamide was obtained from 1.1 mmol of PhSO$_2$CF$_2$SO$_2$F (yield: 78%) in the form of a white solid.

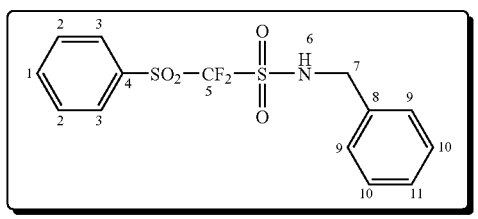

M: 361.38 g·mol$^{-1}$

TLC: $R_f$=0.8 (pentane/AcOEt 4/1)

M.P.: 72° C.

$^{19}$F NMR: δ=−102.36 (s)

$^1$H NMR: δ=4.49 (d, 2H, $^3J_{H6-H7}$=5.8 Hz, H$_7$), 5.62 (t, 1H, $^3J_{H6-H7}$=5.8 Hz, NH), 7.34-7.37 (m, 5H, H$_{Ar}$), 7.64 (m, 2H, H$_2$), 7.82 (m, 1H, H$_1$), 8.02 (m, 2H, H$_3$).

$^{13}$C NMR: δ=48.39 (s, C$_7$), 118.91 (t, $^1J_{C-F}$=331.2 Hz, C$_5$), 127.91 (s, C$_{Ar}$), 128.31 (s, C$_{Ar}$), 128.86 (s, C$_{Ar}$), 129.62 (s, C$_{Ar2}$), 131.03 (m, C$_{Ar3}$), 132.11 (s, C$_{Ar4}$ or C$_{Ar8}$), 135.68 (s, C$_{Ar4}$ or C$_{Ar8}$), 136.50 (s, C$_{Ar1}$).

Example 20

N-benzyl-N-trifluoromethanesulfonyl-(phenylsulfanyl)difluoromethanesulfonamide

The following method was carried out. Added to a ≈0.2M solution of N-benzyl sulfonamide (1 eq.) in dichloromethane obtained according to the method from example 19, kept under an inert atmosphere, was DIEA (1.0 eq.). Triflic anhydride (1.5 eq.) was then added to the mixture at 0° C. This mixture was stirred for 30 min at this temperature, then for 1 h at ambient temperature (monitored by $^{19}$F NMR/CDCl$_3$). At the end of the reaction, the volatile products were evaporated. The residue was dissolved in hot pentane and the supernatant was recovered. After evaporation of the solvent 1.85 g (4.01 mmol) of N-benzyl sulfonimide, which corresponded to the formula below, was obtained in the form of a white solid from 4.5 mmol of PhSCF$_2$SO$_2$NHBn (yield: 89%).

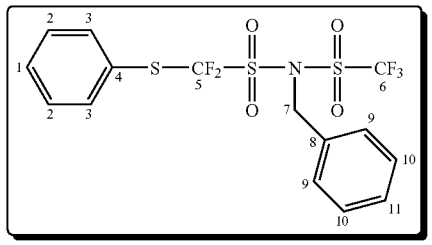

M: 461.45 g·mol$^{-1}$

M.P.: 80-84° C.

$^{19}$F NMR: δ=−72.59 (s, 2F), −72.96 (s, 3F)

$^1$H NMR: δ=5.03 (s, 2H, H$_7$) 7.34-7.56 (m, 8H, H$_{Ar}$), 7.69 (d, 2H, $^3J_{H2-H3}$=7.3 Hz, H$_3$).

$^{13}$C NMR: δ=56.33 (s, C$_7$), 118.99 (q, $^1J_{C-F}$=324.9 Hz, CF$_3$), 122.44 (t, $^3J_{C-F}$=3.0 Hz, C$_{Ar4}$), 128.77 (s, C$_{Ar}$), 128.87 (t, $^1J_{C-F}$=327.9 Hz, CF$_2$), 129.46 (s, C$_{Ar}$), 129.73 (s, C$_{Ar}$), 129.95 (s, C$_{Ar}$), 131.71 (s, C$_{Ar}$), 132.69 (s, C$_{Ar8}$), 137.42 (t, $^4J_{C-F}$=1.1 Hz, C$_{Ar3}$).

Example 21

Lithium N-(trifluoromethanesulfonyl)phenyl-sulfonyldifluoromethanesulfonamide

The following method was carried out. A solution of N-benzyl sulfonimide obtained according to the method from example 20 (1 eq.) in ethanol (C≈0.2M) was stirred for 8 h at ambient temperature, then LiOH.H$_2$O (1 eq.) was added. The mixture was then stirred overnight at ambient temperature, then evaporated to dryness. After evaporation of the volatile products, the residue was dissolved in diethyl ether then filtered. After evaporation of the filtrate and washing of the resulting solid with pentane, 0.20 g (0.49 mmol) of lithium sulfonimide corresponding to the formula below was obtained in the form of a white solid from 0.72 mmol of PhSO$_2$CF$_2$SO$_2$N(Bn)SO$_2$CF$_3$ (yield: 76%).

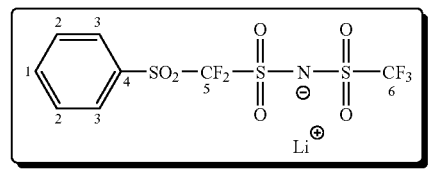

M: 409.26 g·mol$^{-1}$ $^{19}$F NMR: (Acetone-d$_6$) δ=−80.29 (s, 3F), −103.75 (s, 2F).

$^1$H NMR: (Acetone-d$_6$) δ=3.14 (broad s, bound H$_2$O), 7.71 (m, 2H, H$_2$), 7.86 (m, 1H, H$_1$), 8.05 (m, 2H, H$_3$).

$^{13}$C NMR: (Acetone-d$_6$) δ=119.46 (t, $^1J_{C-F}$=329.3 Hz, CF$_2$), 120.79 (q, $^1J_{C-F}$=321.3 Hz, CF$_3$), 130.12 (s, C$_{Ar2}$), 131.62 (s, C$_{Ar3}$), 134.94 (s, C$_{Ar4}$), 136.63 (s, C$_{Ar1}$).

MS: (ESI-MeOH) m/z=402.0 (M$^-$, 100%), 404.0 [(M+2)$^-$, 10%], 810.6 [(2M+Li)$^-$, 9%], 827.5 [(2M+Na)$^-$, 7%].

HRMS: calculated for C$_8$H$_5$F$_5$NO$_6$S$_3$: 401.9199. found: 401.9193.

Example 22

Triethylammonium N-(trifluoromethanesulfonyl)phenyl-sulfanyldifluoromethanesulfonamide The following method was carried out. A solution of N-benzyl sulfonimide (1 eq.) in ethanol (5 ml) was stirred for 8 h at ambient temperature, then triethylamine (1 eq.) was added. The mixture was stirred overnight then evaporated to dryness. After evaporation of the volatile products, the residue was washed with pentane (elimination of supernatant). After drying under vacuum, 0.37 g (0.79 mmol) of the triethylammonium salt corresponding to the formula below were obtained in the form of a yellow oil from 0.9 mmol of PhSCF$_2$SO$_2$N(Bn)SO$_2$CF$_3$ (yield: 88%).

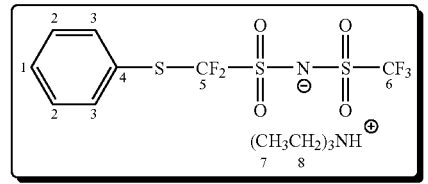

$^{19}$F NMR: δ=−78.62 (s, 2F), −79.09 (s, 3F).

$^1$H NMR: δ=1.33 (t, 9H, $^3J_{H7\text{-}H8}$=7.3 Hz, H$_7$), 3.16 (q, 6H, $^3J_{H7\text{-}H8}$=7.3 Hz, H$_8$), 7.08 (broad s, NH), 7.35-7.48 (m, 3H, H$_{Ar}$), 7.69 (d, 2H, $^3J_{H2\text{-}H3}$=7.3 Hz, H3).

$^{13}$C NMR: δ=8.51 (s, C$_7$), 47.01 (s, C$_8$), 119.77 (q, $^1J_{C\text{-}F}$=321.8 Hz, CF$_3$), 124.27 (t, $^3J_{C\text{-}F}$=2.2 Hz, C$_{Ar4}$), 127.77 (t, $^1J_{C\text{-}F}$=319.7 Hz, CF$_2$), 129.26 (s, C$_{Ar2}$), 130.64 (s, C$_{Ar1}$), 136.86 (s, C$_{A3r}$).

Example 23

Preparation of a Dry Polymer Electrolyte Film

Two dry polymer electrolyte films were prepared from a poly(ethylene oxide) PEO (supplied by Aldrich, M$_w$=5.10$^6$) and from the lithium 2-(phenylsulfanyl)-1,1,2,2-tetrafluoro-N-(trifluoromethylsulfonyl)ethane-sulfonamide from example 10, dried under dynamic vacuum for 48 h. PEO and the sulfonimide were dissolved in acetonitrile in a glovebox under argon. Two tests were carried out with the proportions required to obtain different O/Li ratios (ratio of the number of solvating oxygen units to the number of Li$^+$ ions introduced). Each of the solutions was left stirring overnight. Then it was poured into a glass ring bonded to a teflon surface and left to evaporate overnight. The two films, the thickness of which was between 60 μm and 200 μm, were then dried under dynamic vacuum at 80° C. for 48 h and stored in a glovebox.

The electrolytes were characterized by differential scanning calorimetry DSC at 5° C. per minute from −100° C. to 100° C. The measurement capsules were sealed in a glovebox under argon and kept under argon until the time of the measurement when they were placed under a nitrogen purge in order to prevent any uptake of water which would disturb the measurements. Each sample was subjected to a first rise in temperature followed by a rapid drop and by a second rise in temperature. Since the properties of semi-crystalline polymers largely depend on the thermal history of the material, a good reproducibility of the measurements during the second pass is ensured. The glass transition temperature (T$_g$) is measured at the point of inflexion of the thermogram obtained by DSC, and the melting point is determined at the start of the melting peak. The results are collated in table I below, in which:

O/Li represents the ratio of the number of solvating oxygen atoms to the number of lithium atoms provided by the sulfonylimide in the material obtained by mixing PEO and the sulfonylimide;

Tg$_1$ and Tg$_2$ represent the glass transition temperatures determined respectively during the first and second rise in temperature;

Tf$_1$ and Tf$_2$ represent the melting temperatures determined respectively during the first and second rise in temperature;

ΔH$_{fus1}$ and ΔH$_{fus2}$ represent the enthalpies of fusion determined respectively during the first and second rise in temperature.

TABLE I

| O/Li | Tg$_1$ (° C.) | Tg$_2$ (° C.) | Tf$_1$ (° C.) | Tf$_2$ (° C.) | ΔH$_{fus1}$ J·g$^{-1}$ | ΔH$_{fus2}$ J·g$^{-1}$ |
|---|---|---|---|---|---|---|
| 23.2 | −30.5 | −31.6 | 48.9 | 48.6 | 73.7 | 72.8 |
| 13.9 | −30.5 | −32.7 | 35.6 | 36.6 | 43.4 | 38.5 |

The lithium sulfonylimide decreases the crystallinity and the melting temperature of the polymer electrolytes in comparison with pure PEO. It is deduced therefrom that this salt exerts a plasticizing effect.

The conductivity of dry PEO/PhSCF$_2$SO$_2$NSO$_2$CF$_3$Li polymer electrolytes was measured over three samples for which the O/Li ratio was respectively 30.4, 23.2 and 13.9. The measurements were carried out by electrochemical impedance spectroscopy using a HP 4192A LF impedance analyzer type impedance spectrometer. The electrolyte was then mounted, in a glovebox, between two stainless steel spacers in a sealed Swagelok cell, a spring exerting a constant pressure on the electrolyte. The conductivity measurements were carried out at temperatures decreasing to 55° C. after a stabilization of at least 2 hours at a temperature of 80° C., before the beginning of the measurements, so as to have a good contact with the electrodes. A stabilization time of at least 1 hour was respected for each temperature. After the measurement at 55° C., the cell was cooled to 20° C. The temperature was then increased after keeping the cells at 20° C. for 12 h so as to allow time for a possible crystallization. Several measurements were carried out during the stabilization at 20° C. The measurements from 20 to 50° C. were then carried out at increasing temperature. The temperature was controlled by means of a Vötsch Industrietechnik VTM 4004 thermostated chamber. The thickness of the electrolyte films was measured at the end of the measurement, with a Mitutoyo IP 54 micrometer, so that a possible reduction in thickness due to creep at high temperature results in an undervaluation of the high-temperature conductivities. FIG. 1 summarizes the results obtained for the electrolytes prepared as explained above with the PhSCF$_2$SO$_2$NSO$_2$CF$_3$Li salt.

Example 24

Hexylmethylimidazolium (1-Phenylsulfanyldifluoromethyl)trifluoromethylsulfonylimide Added to a solution of lithium difluorophenylsulfanyl-N-(trifluoromethanesulfonyl)methanesulfonamide prepared according to the method from example 18 (165 mg; 0.44 mmol) in acetone (6 ml) was hexylmethylimidazolium chloride (89 mg; 0.44 mmol) dissolved in distilled water (4 ml). The solution was stirred at ambient temperature for 16 h, then the solvents were removed by evaporation under vacuum. The residue was dissolved in chloroform (20 ml), then washed with distilled water (20 ml). The aqueous phase was extracted with chloroform (2×20 ml) then with dichloromethane (3×20 ml). The organic phases were combined, dried over Na$_2$SO$_4$, and the solvents removed by evaporation under vacuum to give hexamethylimidazolium (1-phenyl-sulfanyldifluoromethyl)trifluoromethylsulfonylimide (186 mg; 79%) in the form of a yellow oil. The formula of the compound is given below.

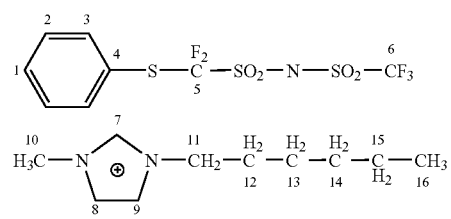

The $^1$H proton, $^{13}$C carbon and $^{19}$F fluorine NMR spectra reveal a clean reaction without trace of residual raw materials. The chemical shifts of the $^1$H protons, $^{13}$C carbon and $^{19}$F fluorine are given in tables II, III and IV below.

$^{19}$F NMR: δ=−78.60 (s, 2F), −79.30 (s, 3F).

$^1$H NMR: δ=0.82 (m, 3H), 1.20-1.36 (m, 6H), 1.79 (m, 2H), 3.87 (m, 3H), 4.10 (m, 2H), 7.25-7.41 (m, 5H), 7.60-7.64 (m, 2H), 8.81 (m, 1H).

Figure 2:
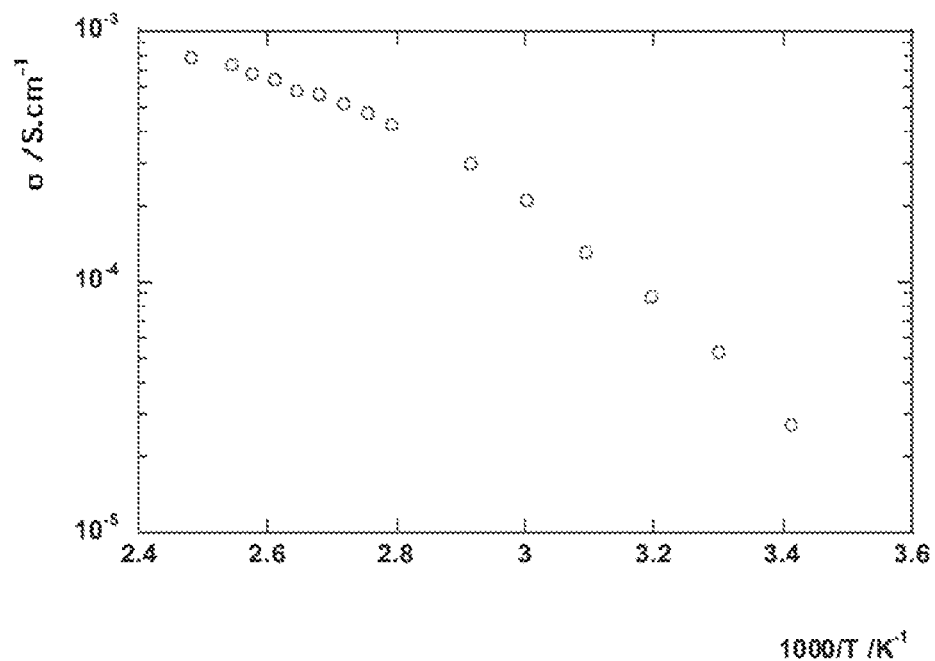
FIG. 2 is a table illustrating the conductivity measurements that were carried out from 20° C. to 130° C. with a stabilization of 2 h at each temperature as per Example 24.

$^{13}$C NMR: δ=13.80 (s), 22.26 (s), 25.71 (s), 30.02 (s), 30.91 (s), 36.27 (s), 50.06 (s), 122.07 (s, CAr), 123.63 (s, CAr), 124.62 (m, CAr4), 129.12 (s, CAr), 130.40 (s, CAr), 136.30 (s, CAr7), 136.88 (s, CAr). The ionic liquid constituted by the imidazolium salt was dried for 3 days under vacuum at 130° C. to remove any trace of water, then stored in a glovebox. Conductivity measurements were carried out on a sample produced by impregnating a macroporous polyethylene/polypropylene separator with the ionic liquid. The macroporous separator was used to provide the mechanical strength. The impregnation took place over 12 hours in a glovebox, the conductivity cell was then assembled. The conductivity measurements were carried out from 20° C. to 130° C. with a stabilization of 2 h at each temperature. The conductivities are given in FIG. 2. The conductivity was 4.7×10$^{-4}$ S/cm at 90° C.

The conductivity measurements of the pure imidazolium salt, without macroporous membrane, were also taken, a conductivity of 6.5×10$^{-4}$ at 90° C. was obtained.

Example 25

Crosslinked Copolymer/PhSCF$_2$CF$_2$SO$_2$NSO$_2$CF$_3$Li Complexes

Electrolytes were prepared according to the following procedure. A macromonomer with an average mass of 8000 g/mol having a polymerizable acrylate functional group at its two ends was prepared from a mixture of ethylene oxide and of propylene oxide. NMR analysis showed that the macromonomer was a random copolymer comprising 75 oxyethylene units per 25 oxypropylene units, the latter giving the macromonomer an amorphous nature.

3 g of the macromonomer were dissolved, in a glovebox, in acetonitrile. Benzoyl peroxide was added thereto in order to achieve a ratio of 5% of peroxide with respect to the acrylate units. After evaporation of the acetonitrile at ambient temperature for 12 hours in a glovebox, the product was heated at 70° C. for 1 h 30 min in a glovebox, to produce the crosslinking.

Disks where then cut from the membrane obtained after crosslinking and the uncrosslinked polymer was extracted with acetonitrile over 15 days, renewing the acetonitrile bath six times.

The disks were then treated under vacuum to remove the acetonitrile and weighed. A solution of acetonitrile containing the amount of salt to be incorporated was then poured over each disk. The disks were then treated under vacuum for 48 h in order to remove the acetonitrile, and stored in a glovebox. The disks were then weighed to determine the amount of salt incorporated. Electrolytes were thus obtained in disk form, in which the O/Li concentration was respectively 14.0, 29.3 and 35.3.

Thermal Characterization

The electrolytes were characterized by DSC (differential scanning calorimetry) at 5° C. per minute from −100° C. to 100° C. The measurement capsules were sealed in a glovebox under argon and kept under argon until the moment of the measurement when they were placed under a dry nitrogen purge in order to prevent any uptake of water which would disturb the measurements. The results are collated in table 10.

The glass transition temperature Tg was respectively −49° C., −47° C. and −36° C. for the O/Li concentrations of 14.0, 29.3 and 35.3.

Conductivity Measurements

The conductivity measurements were carried out for a crosslinked copolymer/PhSCF$_2$CF$_2$SO$_2$NSO$_2$CF$_3$Li having an O/Li ratio of 35.3, by electrochemical impedance spectroscopy using a HP 4192A LF impedance analyzer type impedance spectrometer. The electrolyte was assembled in a glovebox between two stainless steel spacers in a sealed Swagelok cell. A spring exerted a constant pressure on the electrolyte. The conductivity measurements were carried out at decreasing temperature from 90° C. down to −10° C. with a stabilization of 2 hours for each temperature, before the start of the measurements. The temperature was controlled by means of a Vötsch Industrietechnik VTM 4004 thermostated chamber. The thickness of the electrolyte films was measured with a Mitutoyo IP 54 micrometer.

Figure 3:
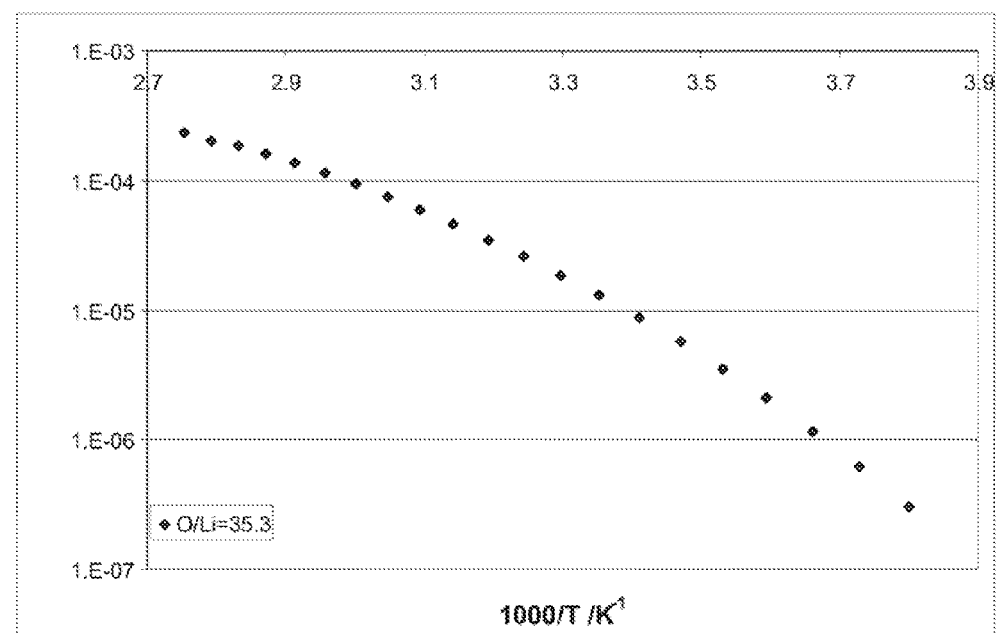
FIG. 3 is a table illustrating the change in the conductivity (S.cm$^{-1}$) as a function of the temperature from Example 25.

FIG. 3 represents the change in the conductivity (S·cm$^{-1}$) as a function of the temperature. Due to the amorphous nature, the conductivities as a function of the inverse of the temperature follow a VTF (Vogel-Tamman-Fulcher) behavior. Thus conductivities of 0.01 mS/cm were obtained from 25° C. and the conductivity exceeded 0.1 mS/cm above 60° C.

The invention claimed is:

1. A method of preparing a sulfonylimide corresponding to the formula (R—SO$_2$—N—SO$_2$R']$_r$M (I), said method comprising the steps of:
    preparing an N-substituted sulfonimide RSO$_2$N(R")SO$_2$R' (II) from RSO$_2$F (III);
    and
    replacing the R" group via a nucleophilic substitution reaction in order to obtain the sulfonylimide (I), R" being a benzyl or trimethylsilyl group, wherein it, in the formulae (I), (II) and (III):
    R represents a group corresponding to the formula Ar—Z-L-;
    R' represents a linear or branched perfluoroalkyl group, preferably a CF$_3$ or C$_2$F$_5$ group, or an Ar'—Z-L- group;
    Z represents a sulfide, sulfinyl or sulfonyl group;
    L represents a group of formula —(CF$_2$)$_n$—CFR$^f$—;
    n is 0 or 1
    R$^f$ represents F or a perfluoroalkyl group having from 1 to 8 carbon atoms;
    Ar and Ar' when R' is an Ar'—Z-L- group, each represent an aromatic group chosen from the group constituted by monocyclic aromatic groups; polycyclic aromatic groups having fused or unfused rings; and heterocyclic aromatic groups that are bicyclic with fused or unfused rings or monocyclic; and
    M is a cation of valence r, chosen from alkali metal, alkaline-earth metal or trivalent or tetravalent metal cations and organic cations chosen from ammonium, phosphonium, imidazolium, guanidinium, piperidinium, pyrrolidinium, pyridinium or quinolinium ions.

2. The method as claimed in claim 1, for preparing a compound (I) in which R' is identical to Ar—Z-L, wherein the compound (II) is obtained by reaction of the compound R—SO$_2$F with a hexamethyldisilazane salt (CH$_3$)$_3$Si)$_2$N$^-$ A$^+$ (A being an alkali metal cation or a quaternary ammonium ion).

3. The method as claimed in claim 1, for preparing a compound (I) in which R' is a perfluoroalkyl group, wherein the compound (II) is obtained by a method comprising the following steps:

reaction of R—SO$_2$F (III) with benzylamine or allylamine in excess;

neutralization by HCl and separation of the R—SO$_2$NH(R″) compound (II′ b);

reaction of the compound (II′ b) with the anhydride (R′SO$_2$)$_2$O, in the presence of a tertiary amine, in order to obtain the compound (II) (R—SO$_2$NSO$_2$R(R″)).

4. The method as claimed in claim 3, wherein the compound (II) (R—SO$_2$NSO$_2$R(R″)) is reacted with a reactant chosen from alkali metal or alkaline-earth metal hydroxides and halides, quaternary ammonium ion hydroxides and halides, alkali metal or alkaline-earth metal alcoholates, quaternary ammonium alcoholates, alkali metal or alkaline-earth metal amides, quaternary ammonium amides, secondary amines, tertiary amines and aliphatic alcohols.

5. The method as claimed in claim 4, wherein the reaction is carried out in the presence of an alcohol.

6. The method as claimed in claim 1, wherein M is an organic cation bearing one or more substituents chosen independently from one another from:
- hydrogen;
- alkyl groups;
- monocyclic aromatic groups; polycyclic aromatic groups having fused or unfused rings; heterocyclic aromatic groups in which the heteroatom is a nitrogen atom, said heterocyclic groups being polycyclic with fused or unfused rings or monocyclic.

7. The method as claimed in claim 1, wherein Ar and where appropriate Ar′ are part of a repeat unit of a polymer chain.

8. The method as claimed in claim 1, wherein Ar bears one or more substituents chosen from:
- halogen atoms, Cl—CH$_2$—, and Q$^1$-O—CH$_2$— groups in which Q$^1$ is H, an alkyl group or an acyl group;
- a hydroxyl group, ether Q$^2$-O—, carboxylic ester Q$^2$C(O)O— and sulfonate Q$^2$-SO$_2$—O— groups, Q$^2$ representing an alkyl group or an aryl group;
- aliphatic or aromatic groups having an optionally substituted ethylenic unsaturation;
- the amino-N(Q$^3$)(Q$^4$)- groups in which Q$^3$ and Q$^4$ each represent, independently of one another, H, an alkyl group, an aryl group, an arylalkyl group or an acyl group;
- trialkylsilyl groups;
- oxirane groups; and
- electron-withdrawing groups chosen from perfluoroalkyl groups, alkylsulfonyl or arylsulfonyl groups, sulfonyl halide groups, and ester, nitrile, cyclic carbonate or nitro groups.

* * * * *